US005789261A

United States Patent [19]

Schwartz

[11] Patent Number: 5,789,261
[45] Date of Patent: Aug. 4, 1998

[54] SOLID PHASE IMMUNOASSAY

[75] Inventor: Cheryl Faye Schwartz, Bensalem, Pa.

[73] Assignee: Temple University of the Commonwealth System of Higher Education, Philadelphia, Pa.

[21] Appl. No.: 741,436

[22] Filed: Oct. 30, 1996

[51] Int. Cl.[6] .................................................. G01N 33/53
[52] U.S. Cl. .......................... 436/518; 436/523; 436/528; 435/288.3; 435/288.4; 435/962
[58] Field of Search ........................ 435/7.1, 288.3, 435/288.4; 436/518, 523, 528

[56] References Cited

U.S. PATENT DOCUMENTS

| | | | |
|---|---|---|---|
| 4,921,809 | 5/1990 | Schiff et al. | 436/531 |
| 5,100,805 | 3/1992 | Ziege et al. | 436/517 |
| 5,132,108 | 7/1992 | Narayanan et al. | 424/78.17 |

FOREIGN PATENT DOCUMENTS

| | | |
|---|---|---|
| 0200381 | 5/1986 | European Pat. Off. |
| 2197720 | 5/1988 | United Kingdom |

OTHER PUBLICATIONS

Seradyn Particle Technology News, vol. 5, pp. 1–6 (Summer 1994).

Kaufmann et al., "Structural Dissection of the Multidomain Kininogens", *The Journal of Biological Chemistry* vol. 268, No. 12, pp. 9079–9091 (Apr. 25, 1993).

Bruil et al., "Poly(ethyleneimine) modified filters for the removal of leukocytes from blood", *Journal of Biomedical Materials Research* 27:1253–1268 (1993).

*Primary Examiner*—Toni R. Scheiner
*Attorney, Agent, or Firm*—Seidel, Gonda, Lavorgna & Monaco, PC

[57] ABSTRACT

Solid supports for solid phase immunoassays comprise polyethyleneimine-coated negatively charged polymeric materials. The combination of negatively-charged polymer support and polyethyleneimine coating serves to eliminate nonspecific adsorption of biological molecules such as high molecular weight kininogen, which have affinity for solid surfaces and which interfere with immunoassays. The negatively charged polymeric support to which the polyethyleneimine coating is applied may advantageously comprise, for example, a carboxylate-modified styrene microparticle. Antigens or antibodies are coupled by covalent coupling agents to the polyethyleneimine coating to form solid phase immunoreagents. Immunoassays for biological molecules such as high and low molecular weight kininogen are provided.

25 Claims, 12 Drawing Sheets

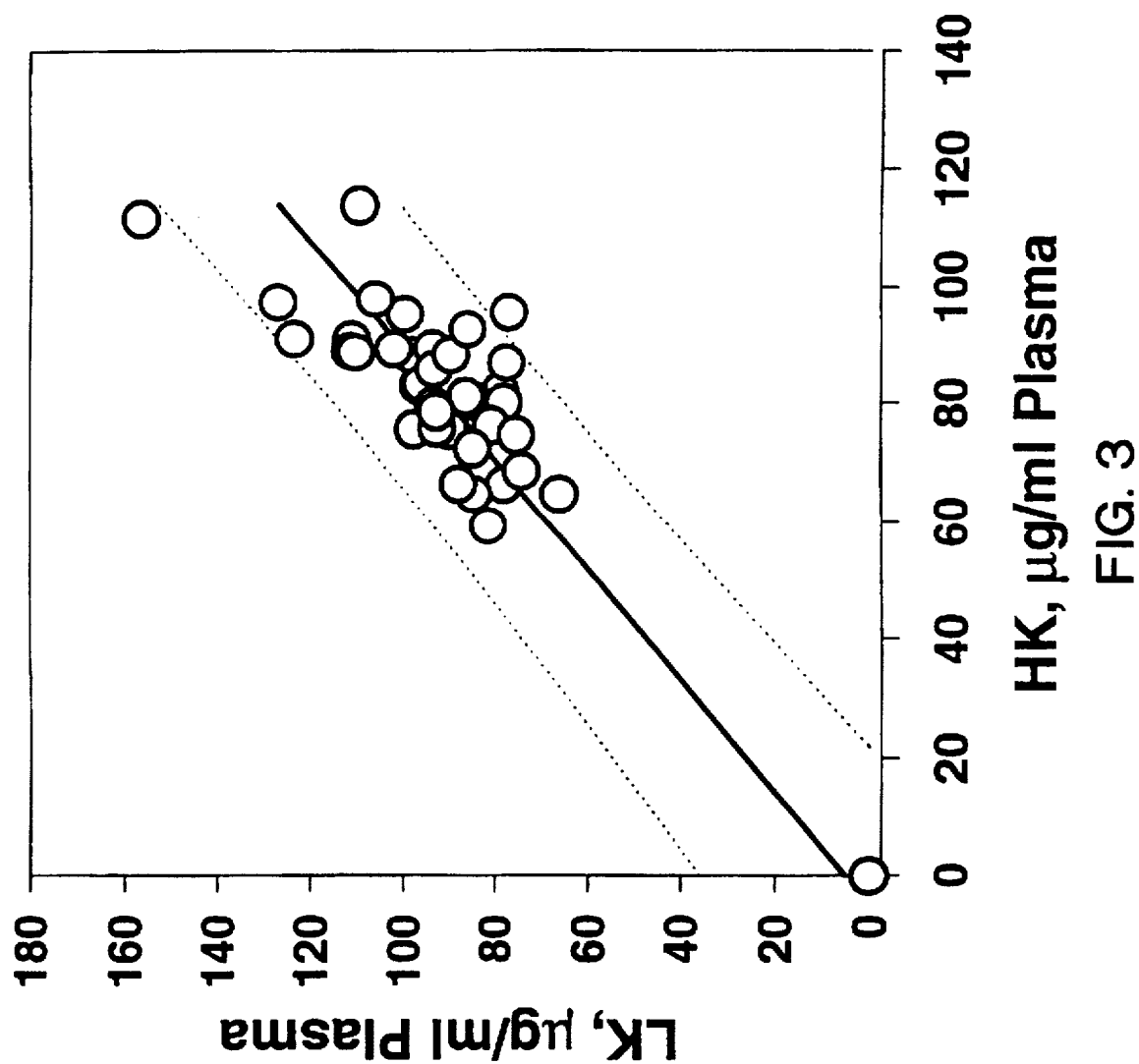

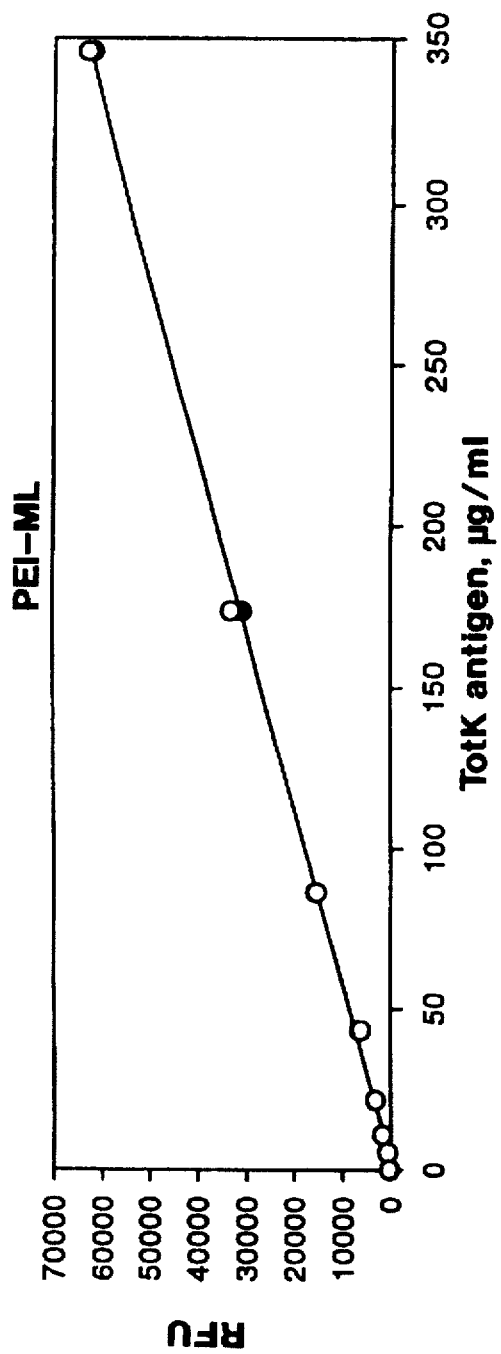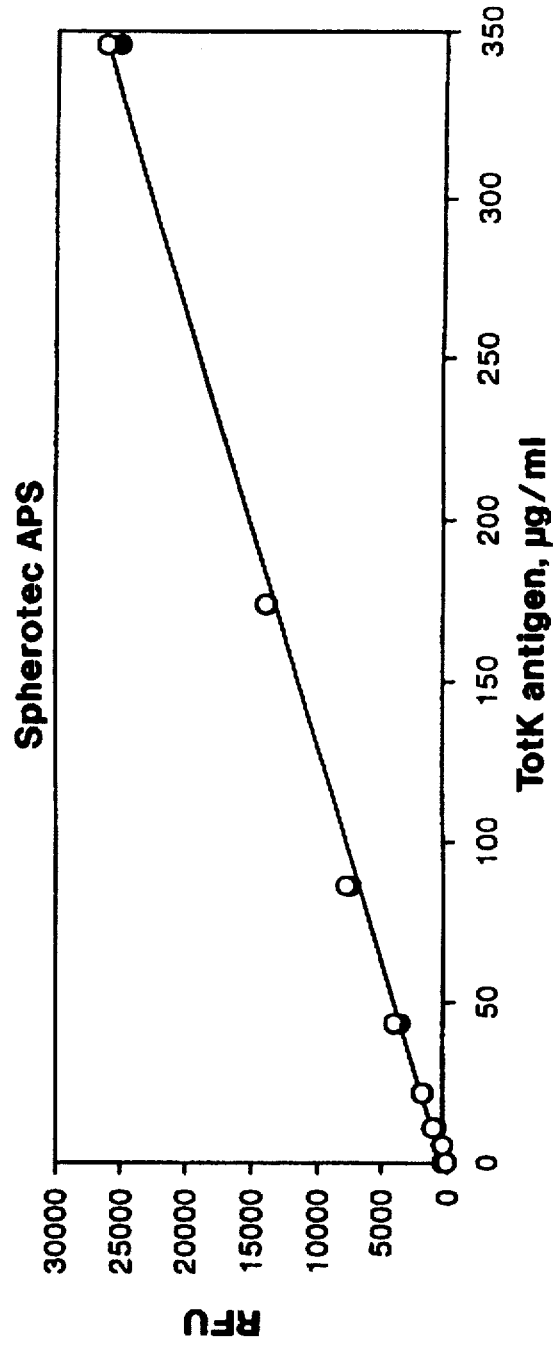

SOLID PHASE IMMUNOASSAY

REFERENCE TO GOVERNMENT GRANT

The invention described herein was supported in part by National Institutes of Health Grant HL 45486. The United States Government has certain rights in the invention.

FIELD OF THE INVENTION

The invention relates to a rapid immunochemical method, using a modified latex surface, for determining concentrations of proteins in biological fluids.

Abbreviations

The following abbreviations are used herein:

| | |
|---|---|
| BSA | bovine serum albumin |
| CML | carboxylate-modified latex |
| EDC | 1-ethyl-3-(3-dimethylaminopropyl)carbodiimide |
| EDTA | ethylenediaminetetraacetic acid |
| ELISA | enzyme-linked immunosorbent assay |
| FCA | fluorescence concentration analyzer |
| FITC | fluorescein isothiocyanate |
| HK | high molecular weight kininogen |
| HKa | activated high molecular weight kininogen |
| HRP | horseradish peroxidase |
| LK | low molecular weight kininogen |
| kDa | kilodalton |
| MAb | monoclonal antibody |
| PBS | phosphate-buffered saline |
| PCFIA | particle concentration fluorescence immunoassay |
| RFU | relative fluorescence units |
| TotK | total kininogen |

BACKGROUND OF THE INVENTION

Immunoassays are currently used to determine the concentrations of various substances in biological fluids. Immunoassays using immobilized immunoreagents are in widespread use for the detection and quantification of biological molecules in samples. An immunoreagent, which may comprise an antibody or antigen, is first immobilized on a solid surface, such as a test tube, microplate, beads or the like. The immobilized reagent is then contacted with an analyte solution containing a complementary immunoreagent, whereby an immobilized immunocomplex is formed between the immunoreagent and complementary immunoreagent. The immobilized immunocomplex can be separated from the unreacted analyte solution, preferably with repeated washing of the immobilized immunocomplex. The separated immunocomplex may be subjected to further processing to quantitate the amount of the immunocomplex. Quantitative methods include, for example, radioimmunoassay (RIA), wherein the amount of the adsorbed immunocomplex may be determined by counting radioactive disintegrations; enzyme-linked immunosorbent assay (ELISA), wherein the adsorbed immunocomplex, which has an enzyme coupled thereto, is contacted with a substrate for the enzyme to produce a detectable product; immunofluorescent assay, wherein the fluorescent intensity of a fluorescent substance linked to the immunocomplex is measured; and chemiluminescent assay wherein the chemiluminescence of a chemiluminescent agent is measured.

Most immunoassay are laborious and/or time-consuming. The development of particle concentration fluorescence immunoassay (PCFIA) (Jolley ME. Baxter, *Pandex Division Research Report Number* 1, 1983), a form of immunofluorescent assay, has added speed and ease to immunoassay. However, currently available microspheres for PCFIA have proven to be unsuitable for the development of an immunochemical assay for certain biological molecules, particularly low molecular weight kininogen (LK) in the presence of high molecular weight kininogen (HK).

LK is one of two kininogens found in human plasma (Margolis and Bishop, *Austral. J. Exp. Biol.* 41: 293–306, 1963) and attached to cells, such as neutrophils (Figueroa et al., *Blood* 79: 954–959, 1992). LK is present in human plasma at a concentration of 93µg/ml and exhibits a molecular weight of 64 kDa. LK is composed of a large heavy chain (59 kDa) and a small light chain (5 kDa). The two chains sandwich the nonapeptide, bradykinin, the most potent vasodilatory substance in humans. The heavy chain is a potent thiol proteinase inhibitor (Sueyoshi et al., *FEBS. Lett.* 182:193–195, 1985). The function of the light chain of LK is not known at this time.

Plasma and tissue kallikreins, as well as other enzymes, can release bradykinin from LK and HK. The release of large quantities of bradykinin into the circulation results in shock which can lead to death.

The heavy chains of HK and LK are identical. Therefore, antibodies against heavy chain immunodeterminants cross-react with both HK and LK. The light chains of HK and LK, which grossly differ by size as well as function, share a segment of 12 amino acid residues at their amino terminus which is derived from the common domain, D4, and differ in their carboxy terminal portions represented by domains $D5_H$ and $D6_H$ (HK) or $D5_L$ (LK). Therefore, antibodies to the complete light chains that include the common amino terminal segment, might partially cross-react with the two types of kininogens. In contrast, antibodies to the unique light chain portions of HK and LK allow discrimination between the two kininogens.

The kallikrein-kinin system has been implicated in several inflammatory diseases such as Systemic Inflammatory Response Syndrome (SIRS) (Nakajima et al., "Kallikrein-kinin system Responses in Septic Shock in Men and Baboons" in *Chemistry and Biology of the Kallikrein-Kinin System in Health and Disease*, Pisano J. and Austen K., editors, DHEW Pub. No. 76–791, 541–544, 1967), periodontal disease (Sakamoto et al., *J. Dent. Res.* 60:6–9, 1981), hereditary angioedema (Schapira et al., *N. Engl. J. Med.* 308:1050–1053, 1983), typhoid fever (Colman et al., *J. Clin. Invest.* 61:287–296, 1978), allergic rhinitis (Proud et al., *J. Clin. Invest.* 72:1678–1685, 1983; Baumgartner et al., *J. Clin. Invest.* 76:191–197, 1985), asthma (Brenner et al., *Allergol. Immunopathol.* 10:453–462, 1982; Abe et al., *Experientia* 23:626–627, 1967) and rheumatoid arthritis (Worthy et al., *Int. J. Exp. Pathol.* 71:587–601, 1990). However, the lack of rapid, simple, reliable assays for the quantification of its components has prevented in depth analyses of the contribution of the kallikrein-kinin system to the pathogenesis of these diseases. In addition, little is known about the variations of the kallikrein-kinin system in the normal population, under physiological situations. Therefore, there was a need for the development of specific assay systems that discriminate between low and high molecular weight kininogen.

Very little is known about the role of LK in health and disease because, until now, there has not been a rapid method to directly quantify LK in biological fluids. Traditionally, LK has been measured indirectly in biological fluids by determining the concentration of HK and LK (total kininogens) with antibodies to their common heavy chains (Kitamura et al., *J. Biol. Chem.* 260:8610–8617, 1985) and then subtracting the concentration of HK, as determined by an antibody to its unique light chain, from the value for total kininogens (Syvanen et al., *FEBS Letters* 129:241–245, 1981; Kerbiriou-Nabias et al., *Br. J. Haematol.* 56: 273–286, 1984; Legris et al., *J. Immunol. Meth.* 168:111–121, 1994). These determinations can result in erroneous estimates for LK if the HK in the sample has either been activated to HKa (Scott e al., *J. Clin. Invest.* 73:954–962, 1984) or cleaved to its inactive form, HKai (Scott et al., *J. Biol. Chem.* 260:10856–10863, 1985).

One such LK assay method includes incubating acidified plasma with trypsin to release bradykinin, first in plasma plus a kininase inhibitor to prevent the destruction of bradykinin after it is released (total kininogens), then incubating a second portion of plasma with a kininase inhibitor and glass powder to activate the contact system thereby releasing bradykinin from HK, and finally, incubating a third plasma sample with glass powder to deplete HK in the absence of a kininase inhibitor (LK), prior to measuring the bradykinin by a bioassay (Uchida and Katori, *Thromb. Res.* 15: 127–134, 1979). The glass powder is assumed to only activate plasma kallikrein that, in turn, releases bradykinin from HK. However, plasma kallikrein can potentially release bradykinin from LK in plasma. Henderson et al., *Blood* 84:474–482, 1994, have observed the rapid disappearance of bradykinin from both LK and HK on neutrophils incubated with purified plasma kallikrein.

Another LK assay method employs the immunochemical technique, radioimmunoassay, to indirectly measure LK. With this assay, HK is detected by using specific antibodies to HK light chain and another antibody to detect the sum of LK plus HK heavy chains (total kininogens). The difference between the values for total kininogens and HK is assumed to represent the concentration of LK in the sample (Kerbiriou-Nabias et al., *Br. J. Haematol* 56: 273–286, 1984). However, this method can give an erroneous value if HK is activated to its cofactor form, HKa, because HK, as determined immunochemically, gives higher values than its unactivated counterpart (Kleniewski et al., *J. Lab. Clin. Med.* 111:93–103, 1988; Scott et al., *J Biol. Chem.* 268:7935–7942, 1993).

Another LK immunochemical assay employs an ELISA using a monoclonal antibody to the common heavy chain of LK and HK that has partial cross-reactivity with HK (Jerabek et al., *Agents Action suppl.* 38:257–266 1992). However, it is doubtful that this assay specifically measures LK.

HK is the contact system cofactor of plasma proteolysis because of its 56 kDa light chain that has the ability to tightly adsorb to negatively-charged surfaces. Because of its ability to form a complex with two of the contact factor zymogens, namely prekallikrein and factor XI, HK can transport these zymogens to the activating surface. This contact system cofactor activity allows HK to be assayed by coagulant activity (Colman et al., *J. Clin. Invest.* 56: 1650–1662, 1975) as well as by an enzymatic assay that measures the conversion of factor XI to its activated form, factor XIa, where the concentration of the cofactor, HK, is the rate limiting determinant in that assay (Scott et al., *Thromb Res.* 48: 685–700, 1987). HK can also be measured, immunochemically, by several methods, including radial immunodiffusion (Scott and Colman, *J. Clin. Invest.* 65: 413–421, 1980), radioimmunoassay (Proud et al., *J. Lab. Clin. Med.* 95: 563–574, 1980), rocket electrophoresis (Bouma et al., *J. Lab. Clin. Med.* 96: 693–709, 1980), and hemagglutination inhibition (Kleniewski and Donaldson, *Proc. Soc. Biol. Med.* 156: 113–117, 1977) because antibodies are easily raised to the large HK light chain. LK, on the other hand, has a small light chain of 5 kDa that does not adsorb to negatively-charged surfaces and its function is, at this time, unknown. Therefore, only antibodies raised against the unique LK light chain or peptides contained therein can specifically capture LK.

In most immunoassays that employ a solid phase, the immobilized immunoreactant, which is either an antibody or an antigen, is passively adsorbed to a solid surface. The solid surface typically comprises, for example, a microparticle or microsphere in the case of a particle assay, or the wells of a polystyrene microplate in the case of an enzyme-linked immunosorbent assay (ELISA). Although most antibodies adhere tightly to plastic surfaces used for these assays, passively-adsorbed antibodies are at risk of being displaced by fibrinogen (Vroman and Adams, *J. Biomed. Mater. Res.* 3:43–67, 1969) and HK (Schmaier et al. *Thromb. Res.* 33: 51–67, 1984) if either or both of these substances are present in the test sample (e.g. plasma). It has been shown that HKa, the active cofactor form of HK (Scott et al., *J. Clin. Invest.* 73: 954–962, 1984) is the form of HK that most readily displaces fibrinogen, IgG, and albumin from surfaces (Brash et al., *Blood* 71: 932–939, 1988). The ability of fibrinogen and/or HK to displace passively-adsorbed antibodies from the solid matrix can result in high coefficients of variation in these assays, especially for determinations of fibrinogen and HK. However, when the primary antibody is covalently attached to the surface, the reproducibility of the assay increases (Scott and Colman, *J. Lab. Clin. Med* 119: 77–86, 1992).

Unfortunately, even when the primary antibody is covalently attached to the solid support, the direct determination of low molecular weight kininogen (LK) in biological fluids has been problematic, primarily due to the interference by HK in the same samples. Two major reasons account for this problem. First, HK and LK have immunologically identical heavy chains and antibodies did not previously exist for the unique light chain of LK. Secondly, HK adsorbs strongly to a variety of common surfaces used in laboratory assays and, if present on the surface, it would react with detector antibodies.

The recent availability of antibodies specific for the unique LK light chain, such as the LKL-1 monoclonal antibody of Kaufmann et al., *J. Biol. Chem.* 268:9079–9091 (1993), have made it possible to immunologically distinguish LK from HK. However, HK's strong tendency to adhere to surfaces is still a source of interference in LK solid phase immunoassay.

What is needed is a solid support material for immunoassays which avoids non-specific adherence of molecules such as HK, which have an affinity for solid surfaces. What is also needed is a solid support for immunoassays which is capable of attaching, per unit of surface area, a high concentration of immunoreagent.

It is therefore an object of the invention to provide a solid support, useful for conducting immunoassays and other types of assays, which avoids nonspecific adsorption of HK and other biological molecules having affinity for solid surfaces.

It is an object of the invention to provide a solid support which allows for a high level of immunoreactant attachment.

It is an object of the invention to provide an immunoassay which employs the aforesaid support.

It is an object of the invention to provide an LK assay which minimizes HK interference.

It is another object of the invention to provide a direct assay for LK, as well as a method for simultaneously assaying HK and LK.

It is another object of the invention to provide a kit for assaying HK and LK, and for carrying out kininogen profiling.

It is an object of the invention to provide a simple, accurate method for developing immunoassays of antigens or antibodies.

It is an object of the invention to provide a method for treating a solid surface to inhibit the surface's ability to activate the contact system in plasma.

These and other objects should be apparent from the following disclosure.

SUMMARY OF THE INVENTION

According to the present invention, a solid support for an immunoassay comprises (a) a microplate comprising a negatively charged polymeric material, and (b) a coating of polyethyleneimine on the microplate.

According to another embodiment, a solid phase carrier for an immunoassay comprises (a) microparticles comprising a carboxylate-modified latex; (b) a coating of polyethyleneimine on the microparticles.

In yet another embodiment, the invention is directed to a solid phase carrier for an immunoassay comprising (a) a solid support; (b) a layer of microparticles coated on the solid support, the microparticles being formed of a negatively charged polymeric material; and (c) a coating of polyethyleneimine on the microparticles.

The invention also provides solid phase immunoreagents for use in immunoassays. In one embodiment, a solid phase immunoreagent comprises (a) a microplate comprising a negatively charged polymeric material; (b) a coating of polyethyleneimine on the microplate; and (c) an immunoreagent immobilized on the microplate by covalent coupling to the polyethyleneimine coating.

According to another embodiment, a solid phase immunoreagent comprises (a) microparticles comprising a carboxy-modified latex; (b) a coating of polyethyleneimine on the microparticles; and (c) an immunoreagent immobilized on the microparticles by covalent coupling to the said polyethyleneimine coating.

In another embodiment, a solid phase immunoreagent for an immunoassay comprises (a) a solid support; (b) a layer of microparticles coated on the solid support, the microparticles being formed of a negatively charged polymeric material; (c) a coating of polyethyleneimine on the microparticles; and (d) an immunoreagent immobilized on the microparticles by covalent coupling to the polyethyleneimine coating.

In another embodiment, a method of treating a negatively charged polymeric surface is provided to inhibit contact activation of plasma by the surface. The surface is coated with polyethyleneimine to inhibit contact activation of plasma brought in contact with the surface.

In each of the above embodiments, the amount of polyethyleneimine comprising the coating should be sufficient to mask the negative charge of the polymeric material comprising the negatively charged polymeric support, e.g., microplate or microparticles, and should also be sufficient, by masking such negative charges, to reduce or essentially entirely eliminate nonspecific adsorption of biological molecules to the support.

The above-described solid phase immunoreagents are useful in carrying out solid phase immunoassays. A first solid phase immunoreagent according to the invention is contacted with a liquid containing or suspected of containing a complementary immunoreagent, whereby an immobilized immunocomplex is formed; and quantitating the immobilized immunocomplex so formed. The immobilized immunocomplex may be detected with a detectably labeled second immunoreagent that is immnunoreactive with the complementary immunoreagent. The second immunoreagent typically comprises an antibody. The immobilized immunocomplex may be washed to remove unbound immunoreagent. The amount of label incorporated into the immobilized immunocomplex is then determined. The detectable label of the detectably labeled second immunoreagent may comprise, for example, a fluorescent label, a radiolabel or an enzyme label.

In another embodiment of the invention, the assay takes the form of a competitive solid phase immunoassay. A solid phase immunoreagent according to the invention is contacted with a liquid containing or suspected of containing a complementary immunoreagent and a known amount of labeled complementary immunoreagent, whereby portions of the labeled and unlabeled complementary immunoreagents are bound to the solid phase immunoreagent. The amount of the labeled complementary immunoreagent bound to the solid phase immunoreagent is quantitated.

The immunoreagent and complimentary immunoreagent together comprise an antigen/antibody pair. In the case where the immunoreagent is an antigen, the complementary immunoreagent is an antibody having binding affinity for the antigen. Where the immunoreagent is an antibody, the complementary immunoreagent is an antigen for which the antibody has binding affinity. In an assay to detect the presence of an antigen in a sample, the immunoreagent will comprise an antibody. Where the assay is designed to detect the presence of an antibody, the immunoreagent will comprise an antigen.

According to one embodiment of the invention, a solid support for a high molecular weight kininogen assay comprises a microplate a coating of a negatively charged polymeric material on the microplate. The coating on the microplate preferably comprises a layer of microparticles formed of a negatively charged polymeric material, most preferably microparticles comprising a carboxylate-modified latex.

According to another embodiment of the invention provides an assay method for high molecular weight kininogen comprising (a) contacting a liquid sample containing or suspected of containing high molecular weight kininogen with a negatively charged solid support to immobilize high molecular weight kininogen in the sample to the solid support;

(b) washing the unbound material from the immobilized sample high molecular weight kininogen;

(c) contacting the immobilized sample high molecular weight kininogen with a detector antibody containing a detectable label bound directly or indirectly thereto, which detector antibody binds high molecular weight kininogen; and (d) assaying the binding of the detector antibody to the immobilized sample high molecular weight kininogen.

Preferably, the negatively charged support comprises a microplate, and the microplate contains a coating of a carboxylate-modified latex or has a negative charge imparted via irradiation, for example, as is common in 96 well tissue culture plates.

According to yet another embodiment, the invention provides a kit for kininogen assays comprising:

(a) a first solid support comprising a negatively charged surface for capturing high molecular weight kininogen;

(b) a second solid support comprising a coating of polyethyleneimine thereon, and a capture antibody specific for low molecular weight kininogen immobilized on said second solid support by covalent coupling to said polyethyleneimine coating; and (c) a third solid support comprising a coating of polyethyleneimine thereon, and a capture antibody specific for kininogen heavy chain immobilized on said third solid support by covalent coupling to said polyethyleneimine coating; and (d) a supply of detector antibody that recognizes both the heavy and light chain of high molecular weight kininogen. The solid supports preferably take the form of microplates or microparticles.

In the aforementioned kininogen assay method and kit, the detector antibody may bear a detectable label. Alternatively, a detectable label is carried by a secondary detector antibody which binds to the detector antibody. The detectable label comprise, for example, a fluorescent label, a radiolabel or an enzyme label. A supply of such secondary detector antibody may be supplied in the kininogen assay kit. In the case where the detectable label is an enzyme label, the kit may further comprise a supply of substrate for the enzyme and a reagent to stop the hydrolysis.

Further optional components in the kininogen assay kit comprise a supply of one or more anticoagulants capable of preventing coagulation of blood samples during collection; a supply of one or more proteinase inhibitors capable of preventing proteolysis of kininogens following sample collection; and a 29 supply of one or more buffers. According to one embodiment, these optional components may be included in a series of containers. For example, the kit may comprise:

(a) a first container comprising a mixture of one or more anticoagulants and one or more proteinase inhibitors;

(b) a second container comprising a buffer composition for diluting samples;

(c) a third container comprising a wash buffer composition for washing the microplates following kininogen capture. The contents of the containers may be in dry powder or liquid form. Preferably, at least the mixture of anticoagulant and proteinase inhibitor contained in the first vial, and the buffer composition contained in the second vial, are in powder form.

By "microplate" is meant a plate, typically made of an optically transparent plastic material, which contains a plurality of wells suitable of holding samples for analysis.

By "nonspecific adsorption" is meant binding by means of a mechanism other than a reaction between an antibody and its cognate antigen. By "biological molecule" is meant any molecule which may be present in the biological sample under analysis. Preferably, the level of nonspecific adsorption is reduced to a level as low as the limit of detection of the assay. Thus, according to the practice of the present invention, the "background" represented by nonspecific adsorption of molecules to the solid support, is reduced essentially to zero, or to a value where the signal to noise ratio is greater than 50:1.

DESCRIPTION OF THE FIGURES

FIG. 3 is a plot of the data from FIG. 1C vs. the data from FIG. 1B. Kininogen-deficient plasma=0. FIG. 3 correlates the levels of HK and LK in the plasma of normal donors.

FIG. 4 correlates the sum of LK plus HK vs. TotK.

FIGS. 6A, 6B and 6C and 6D are standard curves for TotK plasma assays generated from normal pooled plasma using polyethyleneimine-modified latex microspheres (FIG. 6A) and conventional, amino-modified latex microspheres (FIGS. 6B, 6C and 6D).

DETAILED DESCRIPTION OF THE INVENTION

Figure 1A:
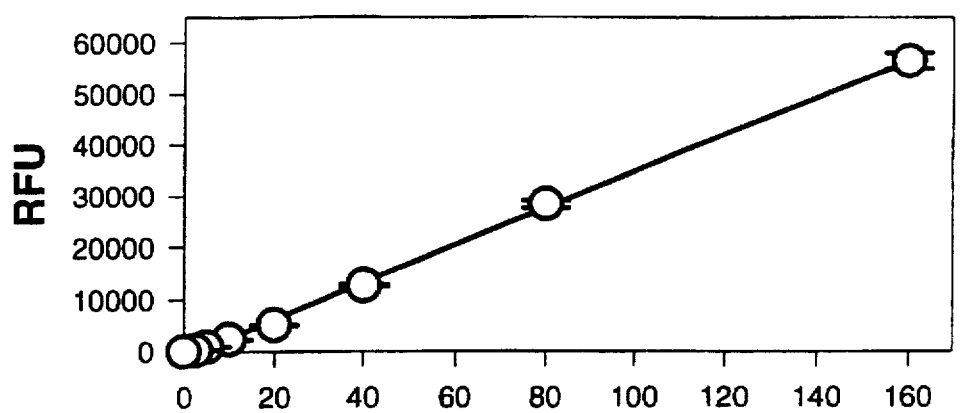
FIGS. 1A, 1B and 1C are, respectively, standard curves for HK, LK and TotK plasma assays of normal plasma. Normal pooled plasma, initially diluted to 1:50 with PCFIA diluent, was serially diluted with PCFIA diluent to generate the standard curves. The ordinate values are expressed as RFU (relative fluorescence units). Each point represents the mean +/− the standard deviation of triplicate determinations.

According to the present invention, polyethyleneimine-coated solid supports are provided, useful in the conduct of solid phase immunoassays, and other types of assays. By "solid phase immunoassay" is meant an assay which utilizes an immunoreagent to capture and detect a complementary immunoreagent, wherein the immunoreagent is bound to a solid support. By "immunoreagent" and "complementary immunoreagent" is meant a pair of reagents which bind to one another by an antibody-antigen binding reaction. It may be appreciated that where the immunoreagent is an antibody, the complementary immunoreagent will comprise an antigen which binds the antibody. It may be appreciated that where the immunoreagent is an antigen, the complementary immunoreagent will comprise an antibody which binds that antigen. The antibody may comprise a polyclonal or monoclonal antibody which binds the target antigen. The antibody may comprise an intact antibody, or fragments thereof capable of binding antigen, including but not necessarily limited to, Fab and F (ab')$_2$ fragments. Hence, as used herein, the term "antibody" includes intact antibody molecules and fragments thereof which retain antigen binding ability. The antigen is typically a protein or peptide antigen, but non-protein antigens, e.g., carbohydrates, lipids, cellular wall components, etc., may also be detected provided the appropriate antibodies are available.

An antibody fixed to a solid support, used to capture an antigen from a patient sample is referred to hereinafter as a "capture antibody". The capture antibody binds to a determinant of the antigen. An antibody not fixed to a solid support, which directly or indirectly bears a detectable label to signal the presence of the captured antigen, is referred to hereinafter as a "detector antibody". The detector antibody binds to another determinant of the captured antigen, which determinant remains exposed on the antigen molecule after the antigen is bound by the capture antibody. It may be appreciated that the detectable label may be affixed directly to the detector antibody (primary detector antibody), or may be fixed to a third antibody which binds to an antigenic determinant on the detector antibody (secondary detector antibody). For example, where the unlabeled detector antibody is sheep anti-human HK, the label may be supplied by donkey anti-sheep IgG. In the case of an ELISA, the secondary detector antibody may thus comprise a conjugate of donkey anti-sheep IgG conjugated to horseradish peroxidase (HRP) (donkey anti-sheep IgG-HRP).

According to one embodiment, the coating material on the solid support comprises polyethyleneimine. By "polyethyleneimine" is meant any polymer which consists of about 85% or more of ethyleneimine (also known as aziridine) monomer. The ethyleneimine monomer has the structure (CH$_2$CH$_2$NH). The term "polyethyleneimine" is meant to include not only homopolymers of ethyleneimine, but also copolymers thereof comprising at least about 85% ethyleneimine units. Preferably, the polymer is a homopolymer of ethyleneimine. A preferred polyethyleneimine has an average molecular weight of about 50,000.

The antigen which comprises either the capturing immunoreagent or the captured complementary immunoreagent may comprise any substance or antigenic determinant of a substance which may be present in a biological sample of interest, e.g., blood, saliva, urine, feces, etc., the detection or quantification of which is desired. According to one preferred embodiment, the complementary immunoreagent is total kininogen (HK plus LK), or LK alone.

The solid support which is modified by polyethyleneimine treatment as described herein comprises a negatively charged polymeric material. The support may be formed entirely of the negatively charged polymeric material, or may comprise only a coating of negatively charged polymer. The surface negative charge of the support permits enhanced coupling of the polyethyleneimine layer which has been found to drastically reduce the level of nonspecific adsorption of biological molecules to the underlying solid support.

The support may take any convenient physical form, such as a membrane, grid, slide, film, stick, tube or particle. According to a particle immunoassay embodiment of the present invention, carboxylate-modified latex particles are the preferred solid supports. In an ELISA embodiment of the invention, the support may take the form of a microplate bearing a coating of carboxylate-modified particles. In the case of non-functionalized supports such as glass, the surface may be coated with a functionalized polymer, most preferably with a carboxylate-modified latex polymer.

Where the support is not itself comprised of a negatively charged polymeric material, a coating of such charged material must be applied. If such a coating is to be applied, then the underlying support may comprise any of the materials which find use as carriers for immunoreagents in solid phase immunoassays. Such materials include glass, metal, and various plastics such as polystyrene, polycarbonate, polyvinyl chloride, polyethylene, polypropylene, silicone resins, and the like, without regard to the requirement of negative charge, as the necessary negative charge is supplied by the added coating of negatively charged polymeric material. The coating carrying the necessary negative charge may be applied, for example, as a suspension of latex particles, e.g., a suspension of carboxylate-modified latex particles such as SERACOAT (Seradyn, Inc., Indianapolis, Ind.).

It should be noted that the polystyrene microplates, which are used in a wide variety of biological assays, are typically formed of virgin polystyrene, which is essentially uncharged. Thus, such standard microplates will not be satisfactory supports according to the practice of the present invention unless coated with a coating of an appropriated negatively charged polymeric material. On the other hand, the added coating of negatively charged polymer is unnecessary in the case of certain modified polystyrenes, which have been modified to impart a negative charge. Tissue culture plates are typically formed from irradiated polystyrene, which is negatively charged. The negative charge assists in cell attachment to the plate. It is also known to modify polystyrene by incorporation of carboxyl groups. Carboxylate-modified styrene microparticles are commercially available from Seradyn Inc., Indianapolis, Ind. The negative charge in these carboxylate-modified polystyrene plates arises from sulfate groups which terminate the polymer chains, adsorbed surfactant used in the process of preparing the microparticles and the carboxylate groups of carboxylate-containing monomers.

The solid support, which is either formed of a negatively charged polymeric material or at least bears a surface coating of a negatively charged polymeric material, is then treated to acquire at least a surface coating of polyethyleneimine. Such coatings include not only polyethyleneimine layers formed by passive physical adherence to the underlying support surface, but also coatings of polyethyleneimine which are chemically fixed to the support surface by reaction with an appropriate coupling agent or agents. Thus, reference herein to a support "coated" or "treated" with polyethyleneimine means not only the application of polyethyleneimine by passive adsorption, but also active chemical coupling of polyethyleneimine to the support surface by means of coupling agents. The preferred form of coupling involves formation of a covalent bond between the support surface and the polyethyleneimine coating. Also considered within the scope of the present invention is the application of polyethyleneimine to particles, such as microscopic particles, and the deposition of such particles as a coating on the surface of a macroscopic support such as a slide or microplate.

Surprisingly, the polyethyleneimine modification of the solid support, when applied to an underlying surface having a negative charge, virtually eliminates non-specific adsorption of molecules such as HK which otherwise adhere to solid surfaces. Yet proteins, such as antibodies or protein antigens, may be easily coupled to the polyethyleneimine-modified surface to serve as the immunoreagent. Moreover, very high immunoreagent loadings, and hence more sensitive immunoassays, are obtained.

According to another embodiment of the invention, polyethyleneimine is used as a coating for negatively charged polymeric materials to inhibit the material's ability to induce contact activation. Factor XII in plasma, when it contacts with a negatively charged surface, will initiate the intrinsic blood coagulation pathway. For this reason, negatively charged polymeric materials cannot be used as supports or vessels for the conduct of assays where plasma is present. According to the invention, the contact activation function of such polymeric materials is substantially reduced, or essentially eliminated, by application of a coating of polyethyleneimine. The polymeric material can now be used as a vessel or a support in a biological assay where plasma is present without fear of spurious results due to triggering of the contact activation system.

The required degree of masking of the negative charge, and therefore the degree of prevention of contact activation, depends upon the time span of the assay employing the solid support. For example, if the support is to be used in a plasma assay which is to be completed within one hour, a modest coating of polyethyleneimine will suffice. If the support is to be used in a plasma assay of several hours duration, then a more extensive polyethyleneimine coating will be required, to ensure that substantially all the surface negative charges are adequately masked. The longer the assay incubation time, the more likely contact activation of the plasma sample will occur, unless steps are taken to block the negative surface charges of the support.

The presence of contact activation in a plasma sample can be conveniently monitored by the appearance of kallikrein, which is released from the zymogen prekallikrein by the action of factor XIIa. The generation of kallikrein can be monitored by the substrate S-2302 (Chromagenix, Inc.), for example.

According to one preferred embodiment of the invention, the solid support comprises microparticles of a polymer having a negative charge. Such particles are generally prepared in the form of polymer latices and take the form of microparticles or microspheres. The term "latex" is intended to have its ordinary meaning, that is, a stable dispersion of a polymeric substance in an essentially aqueous medium. Synthetic latices are generally formed by emulsion polymerization techniques from, e.g., styrene-butadiene copolymer, acrylate resins, polyvinyl acetate, and similar materials.

Most preferably, the polymeric support material to which the polyethyleneimine treatment is applied comprises carboxylate-modified polymer microparticles, the preparation of which is described, for example, in U.S. Pat. No. 5,100,805 to Ziege et al., the entire disclosure of which is incorporated herein by reference. The primary components of such polymer particles can be, for example, a vinyl aromatic monomer, and a vinyl acrylate ester monomer the vinyl aromatic monomer can be styrene, vinyl toluene, t-butyl styrene or mixtures thereof. Styrene is preferred. The vinyl acrylate ester monomer can be a monomer having pendent alkyl ester groups of from one to six carbon atoms, for example. The vinyl acrylate ester monomer can be methyl, ethyl, propyl, n-butyl, s-butyl, or other versions of the acrylate monomer, or versions of a methacrylate vinyl unit, such as methyl methacrylate, ethyl methacrylate, propyl methacrylate, and the like. The particles are prepared by conventional emulsion polymerization methods as described in U.S. Pat. No. 5,100,805.

For carboxylate modification, a carboxylate containing monomer, e.g. acrylic acid, is included in the copolymer comprising the polymeric particles. Acrylic acid is preferred.

Carboxylate-modified microparticles and latex coating compositions are commercially available, for example, from Seradyn, Inc., Indianapolis, Ind. under the trade names CML (carboxylate-modified latex microspheres) and SERA-COAT® (carboxy-modified latex coating material). A representative lot of the CML material is composed of microspheres having a diameter of 0.8 micron containing 0.023 COOH acid milliequivalents per gram.

Polyethyleneimine coating of the immunoassay solid support surface is most advantageously carried out with a suitable coupling agent. The amount of polyethyleneimine applied should be sufficient to completely mask the negative charge on the underlying polymeric support. The amount of polyethyleneimine applied should also be an amount effective to reduce, preferably eliminate, nonspecific adsorption of biological molecules to the negatively charged polymeric support. The coupling agent may comprise any chemical agent which is effective in enhancing the attachment of the polyethyleneimine to the support, e.g. to the particles of the latex. Preferably, the coupling agent acts to covalently link the polyethyleneimine coating to the support. In the case of a carboxylate-modified latex, the preferred coupling agent to fix the polyethyleneimine coating is a carbodiimide, e.g., dicyclohexylcarbodiimide (DDC); 1-ethyl-3-(3-dimethylaminopropyl)carbodiimide(EDC)orhydrochloride of EDC; or 1-cyclohexyl-3-(2-morpholinoethyl) carbodiimide metho-p-toluene sulphonate (CMC). EDC hydrochloride is preferred. The carbodiimide reacts with the carboxylic acid group of the carboxylate-modified latex and activates the carboxyl group, allowing it to be coupled to amino groups in the polyethyleneimine.

The polyethyleneimine coating modification may be carried out by combining the latex particles and the polyethyleneimine, followed by addition of the coupling agent, with stirring, at room temperature. The amount of polyethyleneimine added to the mixture should be sufficient to achieve a uniform coating on the latex particles. The amount of coupling agent is any amount to obtain attachment of the deposited polyethyleneimine onto the latex particle surface. Advantageously, the amount of carbodiimide should exceed the particle's carboxylate content on an equivalent basis, preferably by at least about two fold.

According to a preferred embodiment of the invention, about 0.8µm diameter carboxy-modified latex microspheres ("CML", Seradyn, Inc.) (100 ml of 10% solids) are added to 1% polyethyleneimine with constant stirring. To the mixture, EDC hydrochloride dissolved in water is added and the volume is adjusted with water. The mixture is stirred and the microspheres are then centrifuged and washed with water. The modified microspheres may then be stored at 4° C. in 0.02% $NaN_3$.

Protein immunoreagents, such as antibodies or protein antigens, are easily covalently attached to the polyethyleneimine-modified supports, such as microspheres. The polyethyleneimine treatment does not interfere with protein coupling to the microsphere. The desired protein immunoreagent may be coupled to the polyethyleneimine-modified microspheres, for example, using any of the known coupling agents suitable for the modification and coupling of proteins to solid support materials, provided the coupling does not interfere materially with the ability of the protein to bind its complementary immunoreagent. Any coupling agent which has a first reactive group which can attach to a reactive amino or imino group of the polyethyleneimine, and a second reactive group which can react with and form a covalent bond with a group on a protein molecule, may be used. The coupling agent may comprise the same coupling agent used in carrying out the modification of the latex microspheres to attach the polyethyleneimine coating to the particle surface. According to a preferred embodiment of the invention, the agent for coupling the polyethyleneimine to carboxylate-modified latex particles, and the agent for coupling the immunoreagent to the polyethyleneimine-modified particle, both comprise a carbodiimide, most preferably EDC or EDC hydrochloride.

Following coupling of the immunoreagent to the solid support, the immobilized immunoreagent is contacted with a liquid comprising or containing the biological test sample of interest. The test sample may be a raw biological liquid. More typically, the raw sample is diluted or partially purified prior to assay by conventional techniques known to those skilled in the immunoassay art. The sample and immobilized immunoreagent are incubated for a time sufficient to permit formation of an immunocomplex of the immunoreagent and its complementary immunoreagent. The time for an ELISA should not be less than about 1.5 hours for each incubation step of antibody with antigen. Longer times may be employed. For PCFIA, the time should be not less than 15 minutes. Longer times may be employed. While the temperature and pH of the incubation step may vary, room temperature (23° C.) and a pH between 6.0 and 8.0 are preferred.

After the immobilized immunocomplex is formed, either with or without intervening wash steps, it is contacted with a second immunoreagent which bears a detectable label. The second immunoreagent may comprise either an antigen or an antibody, but typically comprises an antibody. The second immunoreagent is labeled directly with the detectable label, or is labeled indirectly through coupling to another molecule which bears the detectable label. The label may advantageously comprise, for example, a radionuclide in the case of a radioimmunoassay; a fluorescent moiety in the case of an immunofluorescent assay; a chemiluminescent moiety in the case of a chemiluminescent assay; and an enzyme which cleaves a chromogenic or fluorogenic substrate, in the case of an enzyme-linked immunosorbent assay.

Following one or more washing steps to remove any unbound material in an enzyme immunoassay, an indicator substance, for example, a chromogenic substrate, is added which reacts with the enzyme to produce a color change. The color change can be observed visually or more preferably by an instrument to indicate the presence or absence of an antibody or antigen in the sample. For quantification, an instrument is required. For solid phase fluorescence immunoassays, fluorescent labeled moieties can be monitored using excitation at an appropriate wavelength, while chemiluminescent labeled antigens or antibodies can be followed after reaction by chemically activating the chemiluminescent labels to generate light which can be detected by photometric means.

The underlying principle of an immunoassay is that the concentration of the antigen-antibody complex is proportional to the concentration of free antigen and free antibody in the assay medium. Thus, a calibration curve for the determination of an antigen (or antibody) can be constructed by measuring the amount of antigen-antibody complex formed upon addition of varying and known amounts of antigen (or antibody) to a solution containing a fixed and known amount of antibody (or antigen).

The immunoassay may also take the form of a competitive immunoassay.

According to a competitive ELISA or PCFIA, an immunoreagent (e.g., capture antibody), is affixed to a solid support to form a solid phase immunoreagent according to the present invention. Labeled complementary immunoreagent (e.g., labeled antigen) is mixed with the sample, which is then contacted with the solid phase immunoreagent. The labeled and unlabeled antigens will compete for binding to the antibody. The higher the value of the amount of labeled antigen bound to the antibody, the lower the concentration of antigen in the sample.

HK does not adsorb to the polyethyleneimine-modified solid support. Thus, such supports are particularly useful in immunoassays for the direct measurement of substances in human biological fluids where HK may also be present (e.g., plasma). In particular, the polyethyleneimine-modified support materials are useful in the direct measurement of LK in biological fluids. For example, latex microspheres, after covalent attachment of purified antibody specific for LK light chain, may be utilized in a particle concentration fluorescence immunoassay (PCFIA). However, enzyme-linked immunosorbent assay (ELISA) technology may also be used provided the ELISA plates are modified in the same way as the microspheres, and the appropriate antibody or antigens are covalently linked to the microplate surface.

According to a PCFIA for LK determination, polyethyleneimine-modified microspheres, to which a first (capture) antibody specific for LK light chain has been covalently attached, are placed in each well of a 96 well assay plate fitted with a 0.45µm membrane (Idexx Corporation, Westbrook, Me.). The wells of the assay plate contain appropriate dilutions of a reference sample to derive a standard curve. Other wells contain diluted unknown samples. The samples are incubated with the microspheres, at room temperature, until all antigen (LK) in the sample is captured by the antibody on the microspheres (usually 15–20 minutes). Then, without additional washing, a second (detector) antibody, to which a fluorophore has been attached, is added and the mixture is incubated until the detector antibody is bound to all antigen in the sample (usually 10–20 minutes). The plate is then placed in a fluorescence concentration analyzer (FCA) (Idexx Corporation) where the soluble contents of the well are evacuated (20 mm Hg) and then the retained microspheres are washed twice, under vacuum. This procedure completely removes any proteins that are not captured by the microspheres. Because HK is not captured by the capture antibody and fails to adsorb to the antibody-coupled microspheres, it is completely removed during the wash process. The values are expressed as "relative fluorescence units" (RFU). The LK concentration from the unknown samples is determined by comparing the fluorescence value of the sample with the standard curve fluorescence values generated by the reference sample dilutions. Using this method, it is possible to assay 24 samples in triplicate or 40 samples in duplicate together with seven known standards and a buffer control in less than one hour. The LK assay using polyethyleneimine-modified microspheres provides for the specific determination of LK that still contains its light chain. In contrast, when conventional microspheres lacking the polyethyleneimine modification are used as the solid matrix, HK strongly adsorbs to the surface.

The diluent for diluting the samples advantageously comprises, e.g., 10 mM sodium phosphate, pH 7.4, containing 150 mM NaCl, 0.1% Tween 20, 2% bovine serum albumin, and an assortment of proteinase inhibitors described more particularly below.

The capture antibody and/or detector antibody may comprise a polyclonal or monoclonal antibody specific for LK light chain, e.g., the monoclonal antibody "LKL-1" described by Kaufmann et al., *J. Biol. Chem.*

268:9079–9091 (1993). The capture antibody and/or the detector antibody may comprise intact antibody, or fragments thereof capable of binding antigen, including, but not necessarily limited to, Fab and F(ab')$_2$ fragments.

Monoclonal LK antibody may be purified from the ascites of the appropriate LK antibody-producing hybridoma according to conventional antibody purification techniques. For example, antibody may be purified from ascites fluid using commercially available purification kits, such as the IMMUNOPURE® Protein A/G column (Pierce Chemical Company Rockford, Ill.) using the buffers and instructions contained within the kit. After purification, the antibody is concentrated and dialyzed, and stored in buffer.

Hybridomas producing monoclonal antibody specific for LK light chain may be prepared according to the procedure of Kaufmann et al., supra. The entire disclosure of Kaufmann et al. is incorporated herein by reference.

Briefly, a monoclonal antibody having the specificity of MAb LK1-1 may be prepared by first generating, as the immunogen, a conjugate consisting of the peptide Cys-Glu-Tyr-Lys-Gly-Arg-Pro-Pro-Lys-Ala-Gly-Ala-Glu-Pro-Ala-Ser-Glu-Arg-Glu-Val-Ser (SEQ ID NO:1) conjugated to either keyhole limpet hemocyanin or bovine serum albumin as a carrier. The peptide (SEQ ID NO:1) corresponds to amino acid residues 389–409 of human LK. Coupling of SEQ ID NO:1 to the carrier may be carried out via disulfide linkage formation by first treating the carrier protein with maleimidobenzoyl-N-hydroxysuccinimide ester prior to peptide coupling (Liu et al., Biochemistry 18, 690–697, 1979). Murine monoclonal antibody against the peptide conjugate is then generated in BALB/c mice according to standard procedures (Köhler and Milstein, Nature 256, 495–497 1975) with minor modifications described by Hock et al., J. Biol. Chem. 265, 12005–12011, 1990. X63/Ag 8.653 myeloma cells are used for fusion with the harvested immune spleen cells. Colonies producing antibody of the desired specificity are subcloned three times by the limiting dilution method. To induce formation of ascites, syngeneic BALB/c mice may be injected intraperitoneally with 0.5 ml of 2,6,10,14-tetramethylpentadecane (Pristane®, Aldrich Chem. Co.), followed ten days later by application of 5×10$^6$ hybridoma cells in 0.5 ml of RPMI 1640 medium via the same route. Ascites is collected and used for antibody purification.

Figure 1B:
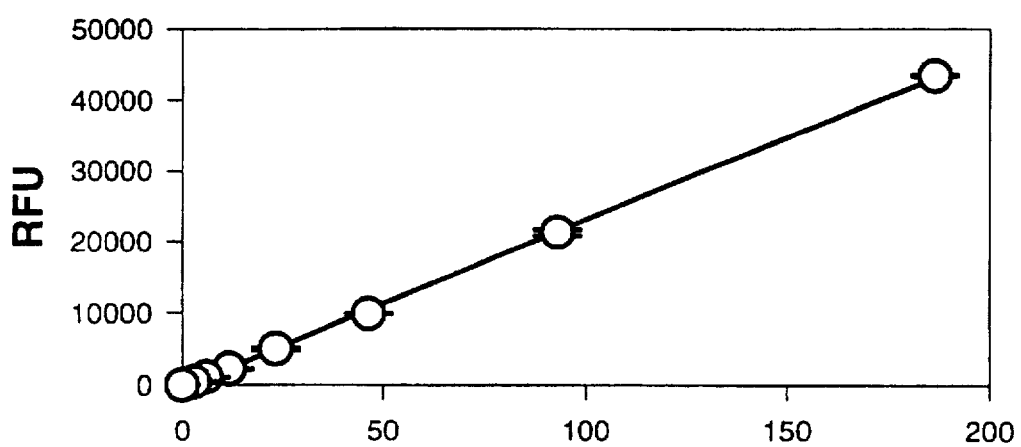
Figure 1C:
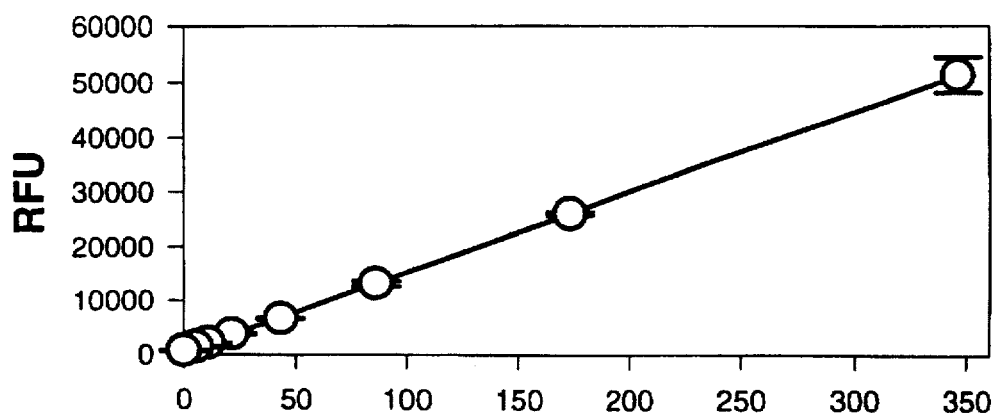

The present invention provides an easy method for the determination of LK in plasma and other biological fluids, as well as a method for the simultaneous evaluation of both HK and LK. Kininogen assays according to the present invention are linear over, at least, a 30-fold range (FIG. 1). Previous descriptions of LK determinations in plasma were, for the most part, indirect measurements. Alternatively, measures had to be taken to separate HK from LK prior to assay because of the problem of HK and LK sharing a common heavy chain. The method of the present invention, on the other hand, provides for the first time, a direct, rapid, quantifiable, measurement of LK, using a monoclonal antibody such as LKL-1.

According to the present invention, the same detector antibody and the same diluted patient sample may be used to assay HK, LK and total kininogen (TotK). This feature permits one to perform "kininogen profiling" studies to assess not only the absolute concentration of the kininogens, but also the specific concentration of kininogens, as well as the extent of kininogen cleavage.

To measure HK, the solid support comprises a conventional negatively-charged microsphere to which no capture antibody need be coupled, since HK is captured by the microsphere by virtue of its ability to adhere to negatively-charged solid surfaces. Preferably, the microsphere comprises a carboxylate-modified latex. The sample is contacted with the microspheres, and HK binds to the negatively charged surface. Washing the microspheres removes the unbound material and leaves immobilized HK on the particle surface.

For the TotK assay, the solid support comprises polyethyleneimine-modified microspheres to which an antibody has been attached which recognizes the heavy chains of both HK and LK. For example, the antibody may comprise monoclonal antibody 2B5, obtained from hybridoma ATCC #HB-8963, the preparation of which is described in U.S. Pat. No. 4,908,431. The entire disclosure of U.S. Pat. No. 4,908,431, is incorporated herein by reference. To measure LK, the support comprises polyethyleneimine-modified microspheres to which is attached an antibody which is specific for LK light chain, and does not recognize HK, such as the LK-1 MAb.

According to an ELISA based upon the same principles, a carboxylate-modified latex of smaller particle sizes, 0.1 µm in diameter (SERACOAT® TC3X, Seradyn, Inc.) is used to coat the wells of a 96-well microplate. The plate is dried. For LK and TotK assays, a 1% solution of polyethyleneimine in 10 mM Na$_2$PO$_4$, pH 6.0+0.5 mM EDTA is prepared. EDC.HCl (9.6 mg/ml) was added and the mixture is then immediately added to the latex-coated microplate. The wells are completely filled with the solution and allowed to stand to fix the polyethyleneimine coating on the carboxylate-modified latex particles. The plate is then washed with deionized water and dried. For a TotK ELISA, the immunoreagent coupled to the latex/polyethyleneimine-coated plate comprises an MAb, such as MAb 2B5, which recognizes both HK and LK heavy chains. For an LK ELISA, the immunoreagent comprises an MAb such as MAb LKL-1 which is specific for LK light chain. The antibody is applied, at a concentration of 5 µg/well, to each well in a solution containing EDC.HCl as a coupling agent, followed by incubation for at least about two hours. The wells of the assay plate are filled with appropriate dilutions of a reference sample to derive a standard curve. Other wells contain diluted unknown samples. After 1.5 hours of incubation at room temperature, the plates are emptied and washed with wash buffer. The wash buffer may comprise, for example, 10 mM sodium phosphate, pH 7.0, containing 0.5 M NaCl, 0.2% NaN$_3$ and 0.1% polysorbate 20 (Tween 20). As a primary detector antibody, sheep anti-human HK diluted in buffer (200 µl diluted 1:1500 in buffer) is placed in each well and the plates are incubated for 1.5 hours, then washed. As a secondary detector antibody, donkey anti-sheep IgG to which the enzyme horseradish peroxidase has been conjugated (anti-sheep IgG-HRP) is diluted in buffer and applied to each well. Alkaline phosphatase cannot be used because there are phosphatases in human plasma that can hydrolyze the substrate and cause a background. After room temperature incubation for two hours, the plates are washed and then enzyme substrate is added to each well. The optical density of the hydrosylate is determined with respect to standards to provide the TotK or LK concentration in the unknown samples.

HK in biological fluids can adsorb to negatively charged surfaces without the need for a capture antibody. Thus, an HK ELISA may be conducted without the need for an immobilized capture antibody, or a polyethyleneimine coating on the ELISA microplate. Carboxylate-modified latex of smaller particle sizes, e.g., the 0.1 µm diameter SERA- COAT® TC3X particles may again be used to coat the wells of a 96-well microplate. The carboxylatemodified latex provides a surface negative charge which binds HK. The microplate may comprise an uncharged material, such as virgin polystyrene, or a modified polystyrene, which has been modified to impart a negative charge. If the microplate comprises a negatively charged material, then the surface coating of carboxylate-modified latex may be omitted. However, to ensure that the microplate surface acquires a surface negative charge sufficient to result in HK capture, coating of the plate with the latex is preferred, even in cases where the microplate may already comprise a negatively charged material.

For the HK ELISA, the wells of the microplate are filled with appropriate dilutions of a reference standard to derive a standard curve. Other wells contain diluted unknown samples. After 1.5 hours of incubation at room temperature, the plates are washed with wash buffer and contacted with sheep anti-human HK as a primary detector antibody, donkey anti-sheep IgG-HRP as the secondary detector antibody, and enzyme substrate, as above. The ELISA is completed by determining the optical density of the enzyme hydrosylate, and comparing the value with standard values to provide the HK concentration in the unknown samples.

The kininogen assay embodiments of the invention are amenable to practice in kit format. Such a kit, suitable for HK, LK and TotK assays, contains solid supports, preferably in the form of microplates (for ELISA) of microspheres (for PCFIA). A microplate or microsphere for conducting an HK assay has a negatively charged surface for capturing HK. A microplate or microsphere for an LK assay carries a coating of polyethyleneimine and a capture antibody specific for LK. A microplate or microsphere for TotK assay carries a coating of polyethyleneimine and a capture antibody specific for kininogen heavy chain. The capture antibodies are covalently coupled to the polyethyleneimine coating on the microplate or microsphere.

The kininogen assay kit further contains a supply of detector antibody which recognizes both the heavy and light chain of HK. The detector antibody can thus be used to quantitate the kininogen captured in any of the three kininogen assays -HK, LK or TotK. Appropriate polyclonal antisera to whole HK, that recognizes both the heavy and light chains of HK and the light chain of LK, is commercially available (The Binding Site, Ltd., San Diego, Calif.). A detectable label is carried by the detector antibody. For PCFIA, the detector antibody may comprise anti-human IgG-FITC, for example. Alternatively, the detectable label is carried by a secondary detector antibody which binds the primary detector antibody. A supply of the secondary detector antibody, e.g., goat anti-sheep IgG-HRP, is thus optionally included in the kit for ELISA.

An ELISA kit may further contain a supply of substrate for the enzyme, e.g., HRP, and a reagent to stop hydrolysis of the substrate by the enzyme, e.g., citric acid or $H_2SO_4$.

The kininogen assay kit further optionally includes appropriate auxiliary reagents for collecting, storing and assaying patient samples. These reagents are formulated to stabilize patient samples, to prevent clotting, and to prevent cleavage of kininogens by proteinases in the test sample. One such auxiliary reagent is a mixture of proteinase inhibitors and anticoagulant, such as described in Example 2A, below. While the preferred cocktail contains acid-citrate-dextrose (ACD) as an anticoagulant, other suitable anticoagulants include heparin or oxalic acid. Patient blood samples are advantageously drawn into a plastic syringe containing an amount of proteinase inhibitor cocktail sufficient to prevent coagulation and kininogen cleavage in the sample. A sufficient amount is approximately one tenth of the volume of the blood sample being drawn. While the proteinase inhibitor cocktail is described herein as a liquid, it may be appreciated that the cocktail can be formulated in dry powder form, which is then diluted with an appropriate amount of sterile water to reconstitute the liquid form prior to use.

Another auxiliary reagent for the kininogen assay kit comprises a diluent buffer for diluting patient samples. The diluent buffer is advantageously based upon phosphate buffered saline, and includes stabilizers such as polysorbate 20 (Tween 20), bovine serum albumin, and preferably a small amount of proteinase inhibitor cocktail to ensure that the proteinases in the patient sample are not activated upon dilution of the sample with the diluent buffer. The preparation of a representative diluent buffer ("PBS-TBI") is set forth in Example 1C, below. While the diluent buffer is described herein as a liquid, it may be appreciated that the buffer can be formulated in dry powder form, which is then diluted with an appropriate amount of sterile water to reconstitute the liquid form prior to use.

Another auxiliary reagent for the kininogen assay kit comprises a wash buffer for washing unbound material from microplates or microspheres following capture of kininogens. A representative wash buffer consists of 10 mM sodium phosphate, pH 7.0, containing 0.5 M NaCl, 0.02% sodium azide and 0.1% polysorbate 20. The wash buffer is advantageously stored in the kit as a 10 X concentrate, which is then diluted 1:10 with sterile water prior to use. Alternatively, the wash buffer may be stored in dry form, and diluted with an appropriate amount of sterile water to reconstitute the liquid form prior to use.

Patient blood samples (about 5 ml) for the kininogen assays may be collected into plastic syringes containing 0.5 ml of proteinase inhibitor cocktail. The blood should be immediately centrifuged to remove cells. The cell-free plasma may be stored frozen at –70° C.

The following non-limiting examples are intended to illustrate the assay of the present invention.

EXAMPLE 1

Preparation of Polyethyleneimine-modified

Carboxy-modified Latex Microspheres

Ten grams (100 ml of 10% solids) of 0.8 μm carboxy-modified latex microspheres formed from a copolymer of styrene and acrylic acid (CML, Seradyn, Inc. Indianapolis, Ind.) were added to 60 ml of 1% polyethyleneimine (Sigma Chemical Co.) in a glass vessel with constant stirring. Then, 168 mg of 1-ethyl-3-(3-dimethylaminopropyl)carbodiimide (EDC) hydrochloride dissolved in water, was added. The volume was brought to 200 ml with water and the mixture was stirred for two hours. The microspheres were then centrifuged and washed twice with water. The modified particles were stored at 4° C. in 0.02% $NaN_3$.

EXAMPLE 2

Low Molecular Weight Kininogen Antibody

Coupling to Polyethyleneimine-modified Latex Microspheres

Microspheres for the direct measurement of LK were prepared as follows with the monoclonal antibody LKL-1, which is directed against the LK light chain, as the capture antibody.

A. Purification of LKL-1 Monoclonal Antibody

Monoclonal antibody LKL-1 (Kaufmann et al., *J. Biol. Chem.* 268:9079–9091, 1993) was purified from ascites on an IMMUNOPURE® Protein A/G column (Pierce Chemical Company, Rockford, Ill.) using the buffers and instructions contained within the kit. LKL-1 is a mouse antibody specific to human LK light chain. After purification, the antibody was concentrated and dialyzed in a CENTRICON 30 concentrator (Amicon Corp., Danvers, Mass.). The buffer was exchanged with 10 mM sodium phosphate, pH 6.0+0.5 mM EDTA. Portions (1.5 ml) of the purified antibody were frozen until needed. It was necessary to completely remove any traces of sodium azide ($NaN_3$) from the buffer in which the protein was stored as it interfered with the subsequent covalent coupling.

B. Preparation Of Proteinase Inhibitor Cocktail

Benzamidine (100 mM), 400 µg/ml hexadimethrine bromide, 2 mg/ml soybean trypsin inhibitor, 20 mM EDTA, 263 µM leupeptin (all from Sigma Chemical Co.), 1 mM Phe-Phe-Arg-chloromethyl ketone (PPACK II) and 20 mM [4-(2-aminoethyl)-benzenesulfonylfluoride.HCl (AEBSF) (both from Calbiochem, La Jolla, Calif.), were dissolved in the anticoagulant acid-citrate-dextrose (ACD) to make proteinase inhibitor cocktail for blood collection.

C. Preparation of PBS-Tween, PBS-Tween-BSA and PBS-TBI

Phosphate buffered saline containing Tween ("PBS-Tween" was composed of 10 mM sodium phosphate, pH 7.0, 150 mM sodium chloride, 0.02% $NaN_3$, and 0.1% Tween 20 (Sigma Chemical Co.). "PBS-Tween-BSA" was prepared by adding 5 ml of 10% bovine serum albumin to 45 ml PBS-Tween. A diluent, "PBS-TBI", was prepared consisting of PBS-Tween containing 1% BSA and 1% proteinase inhibitor cocktail.

D. Coupling of LKL-1 Monoclonal Antibody to Polyethyleneimine-modified Latex Microspheres Covalent linkage of the mouse anti-human LK monoclonal antibody LKL-1 to polyethyleneimine-modified latex microspheres was carried out as follows. In a 50 ml conical screw cap polypropylene centrifuge tube were placed 32.6 ml $H_2O$, 2 ml of 100 mM sodium phosphate, pH 6.0+5 mM EDTA, and 2 ml of 8% (w/vol.) polyethyleneimine-modified microsphere prepared according to Example 1. The contents were briefly mixed before adding 1.2 ml of monoclonal antibody LKL-1 (2.71 mg/ml in 10 mM sodium phosphate, pH 6.0+0.5 mM EDTA). The tube was placed on a nutator for 30 minutes. If the particles started to form large aggregates, then the mixture was subjected to several bursts of sonication. Next, 200 µl of 1 M EDC hydrochloride was added and the tube was immediately closed and mixed before placing on a nutator overnight. The final antibody concentration was approximately 85 µgl/ml. The next day, the tube was centrifuged and the supernatant was removed. Twenty ml of 10% bovine serum albumin, in the phosphate buffer mentioned above, was added to the microspheres to block unreacted sites as well as to stabilize the particles. The tube was vigorously mixed to thoroughly resuspend the coated particles and then placed on a nutator for 30 minutes. The microspheres were then centrifuged and washed twice with phosphate buffered saline containing 0.1% Tween 20 (Sigma Chemical Co. St. Louis, Mo.). The coated microspheres were then brought to a final volume of 60 ml in PBSTween-BSA containing 0.02% $NaN_3$ and stored at 4° C. The coated microspheres were stable for at least 12 months. Sixty ml of the microspheres is sufficient to perform 3,000 LK determinations.

E. Determination of Coupling Efficiency of LKL-1 Antibody to Polyethyleneimine-modified Latex Microspheres After the antibody was coupled to the polyethyleneimine-modified microspheres, both the supernatants and the microspheres were assayed for mouse IgG by PCFIA (Scott and Colman J. *Lab. Clin. Med* 119: 77–86, 1992), to determine the efficiency of the coupling of LKL-1 to the microspheres. Microspheres coated with mouse IgG were used to capture the IgG in the supernatants. Anti-mouse IgG F(ab')$_2$ labeled with fluorescein isothiocyanate (FITC) (Sigma Chemical Co.) was used as the detector. Standards were prepared from normal mouse IgG (Pierce Chemical Co.). LKL-1-containing microspheres were diluted 1:30 before they were added to the assay plate. Coupling efficiency was similar for each batch of particles prepared. The concentration of LKL-1 in the final microsphere suspension was 12.12 +/−1.49 µg/ml microsphere suspension.

F. Binding Capacity of Microsphere for Low Molecular Weight Kininogen Twenty µl of the microsphere suspension, containing 243 ng of MAb LKL-1, was able to bind at least 42 ng of LK via its light chain and produce a linear standard curve (FIG. 1B) Twenty percent of the antibody is occupied by antigen (LK) at the top of the standard curve. The five-fold molar excess of antibody on the microspheres to antigen in the sample ensures that all antigen will be bound to the solid matrix.

EXAMPLE 3

Total Kininogen Antibody Coupling to Polyethyleneimine-modified Latex Microspheres Microspheres for the simultaneous direct measurement of HK and LK were prepared as follows with a monoclonal antibody, 2B5, directed against the common heavy chains of HK and LK.

A. Purification of 2B5 Monoclonal Antibody and Coupling to Microspheres

Monoclonal antibody 2B5, obtained from hybridoma ATCC #HB-8963 (U.S. Pat. No. 4,908,431) was purified from ascites according to the procedure of Example 2, part A. MAb 2B5 is a mouse monoclonal antibody directed against the common heavy chains of human HK and LK. MAb 2B5 was covalently linked to polyethyleneimine-modified microsphere prepared according to Example 1, in the same manner as Example 2, part D, except that the final volume of microspheres, after coupling, was brought to 40 ml. Coupling efficiency of the antibody to the microsphere was determined as in Example 2, part E. The concentration of MAb 2B5 was 7.99 +/−3.69 µg/ml. Approximately 2,000 total kininogen determinations could be performed with 40 ml of these microspheres.

B. Binding Capacity of Microsphere for Total Kininogen

Twenty µl of the microsphere suspension, containing 160 ng of MAb 2B5 was able to bind at least 58 ng LK and HK via their heavy chains and produce a linear standard curve (FIG. 1C) Thirty-seven percent of the antibody is thus occupied by antigen (LK or HK) at the top of the standard curve. The 2.75-fold molar excess of antibody on the microspheres to antigen in the sample ensures that all antigen will be bound to the solid matrix.

EXAMPLE 4

Kininogen Particle Concentration Fluorescence Immunoassay of Normal

Plasma with Polyethyleneimine-modified Latex Microspheres

A. Preparation Of Reference Plasma for PCFIA

Blood (4.5 ml) was collected from each of 20 healthy donors directly into plastic syringes containing 0.5 ml proteinase inhibitor cocktail. The blood was immediately mixed and centrifuged at 20° C. at 2000×g for 5 minutes. After removing erythrocytes, the plasma was re-centrifuged at 12,000×g for 10 minutes. Aliquots of the cell-free plasma were frozen at −70° C. One hundred µl of plasma from each donor was pooled and used as reference plasma. The reference plasma was diluted 1:50 in PBS-TBI. Serial dilutions of the plasma were prepared using PBS-TBI. It was essential to prepare reference plasma from blood that had been collected into inhibitor cocktail because commercial reference plasma was found to be cleaved and, therefore, unsuitable for use as a standard.

B. Preparation of Tracer Antiserum for PCFIA

A polyclonal antibody to whole HK (that recognizes both heavy and light chains of HK and the heavy chain of LK), labeled with FITC was purchased from The Binding Site, Ltd., San Diego, Calif. The same antibody, unlabeled, was also used and was combined with the FITC-labeled antibody by adding twenty µl of the FITC-labeled antibody (10 mg/ml), 100 µl of unlabeled antibody (14 mg/ml) and 7820 µl PBS-Tween-BSA to a glass vial. The tracer antiserum could be stored at 4° C. for up to 2 weeks.

C. Direct PCFIA Determination of LK in Plasma of 38 Normal Donors

Figure 2C:
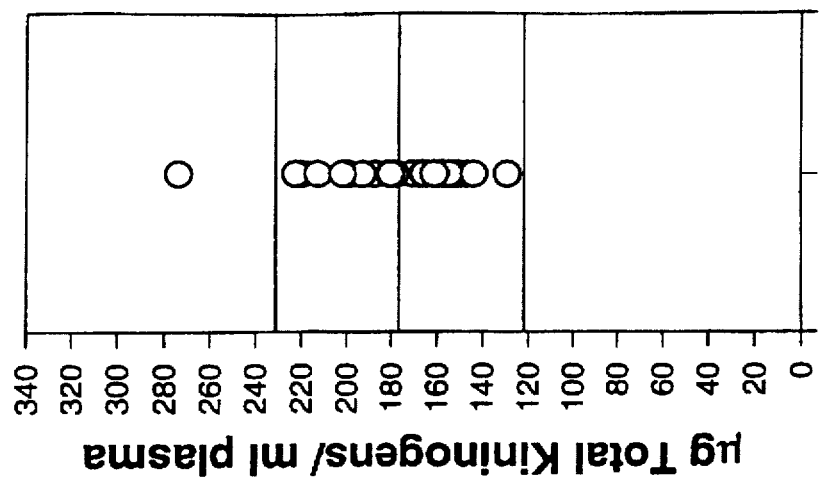
FIGS. 2A, 2B and 2C are, respectively, PCFIA measurements of HK, LK and TotK in the plasma of 38 normal donors. Reference lines are located at the means, + and −2 standard deviation for each.
Figure 2B:
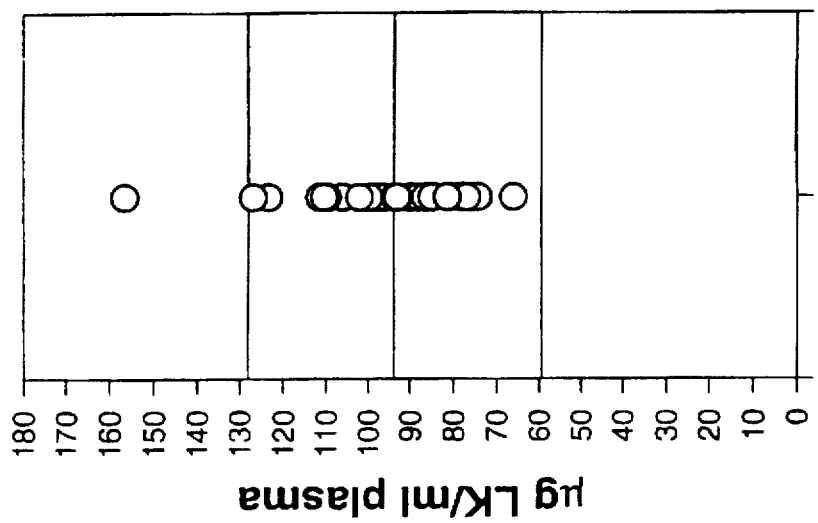

PCFIA was performed as follows, in triplicate, in 96 well assay plates fitted with a 0.45 Mum membrane (Idexx Corporation). Twenty µl of LKL-1-coated microspheres prepared according to Example 2 were placed in each well followed by 10 µl of reference plasma diluted in PBS-TBI (ranging from 1:50 to 1:3200) or 10 µl of unknown plasma samples from 38 normal donors that had been diluted 1:100 in PBS-TBI. Normal pooled plasma containing 93 µg/ml LK was used so that the value of 186 µg/ml was chosen for the 1:50 diluted reference plasma. PBS-TBI was used as the blank. After 20 min, 20 µl of tracer antiserum was added and the mixture was incubated an additional 20 minutes. The plate was then placed in a Fluorescence Concentration Analyzer (FCA) (Idexx Corporation) where the wells were evacuated (20 MM Hg). The microspheres were washed twice, under vacuum, with 10 mM sodium phosphate, pH 7.0, containing 0.5 M NaCl and 0.02% sodium azide (Wash Buffer). The plate was read on the FCA and the data were analyzed by Winplate software, version 1.1 (Idexx Corporation) using an IBM compatible 386DX-40 computer equipped with Windows for Workgroups 3.11 or WINDOWS 95 software (Microsoft Corp. Redmond, Wash.). The curves were fitted by the Winplate version 1.1 software and the averaged values for the triplicate or duplicate determinations were automatically calculated from the standard curve. Sigma Plot for Windows, versions 1.1, 2.0 and 3.0, as well as Sigma Stat for Windows, version 1.0 (Jandel Corporation), were employed for data analysis and graphing. The standard curve for LK generated with the normal pooled plasma appears as Fig. 1B. LK could be detected in the unknown samples by PCFIA between 50 and 1900 ng/ml. The assay was liner in this range. The LK concentration in 38 normal donors ranged from 61 to 156 Ag/ml with a mean of 93 µg/ml (FIG. 2B).

D. Direct PCFIA Determination of Total Kininozen (HK and LK Heavy Chain) in Plasma of 38 Normal Donors Because HK and LK share a common heavy chain and because MAb 2B5 is directed towards the heavy chain (Schmaier et al., *J. Biol. Chem.* 262:1405–1411, 1987), using 2B5 as the capture antibody results in the simultaneous measurement of both HK and LK (or total plasma kininogens). For brevity, this determination is called, "TotK" (for total plasma kininogens). TotK-PCFIA was performed as described above for LK-PCFIA except that 20 µl of 2B5 MAb-coated microspheres (Example 3) were substituted for the LKL-1 MAb-coated microspheres used in the LK-PCFIA. A pool of normal plasma containing 173 µg/ml TotK was used as the standard. The value of 346 µg/ml was chosen for the 1:50 diluted reference plasma. The standard curve for TotK generated with the normal pooled plasma appears as FIG. 1C. TotK could be detected in the unknown samples by PCFIA between 100 and 3500 ng/ml. The assay was liner in this range. TotK in the 38 normal donors ranged from 129 to 274 µg/ml with a mean of 176 µg/ml (FIG. 2C).

E. Direct PCFIA Determination of HK in Plasma of 38 Normal Donors

HK-PCFIA (FIG. 1A) was performed as previously reported (Scott and Colman, *J. Lab. Clin. Med.* 119:77–86, 1992) with the following modifications. HK adheres to carboxylate-modified latex even in the absence of a capture antibody coating. LK does not adhere to such microspheres in the absence of an antibody coating specific for LK. Thus, for the HK-PCFIA assay, uncoated carboxylate-modified latex microspheres (CML, Seradyn, Inc,) were used as the solid support to capture HK instead of the C11C1 MAb-coated microspheres of Scott and Colman, supra.

Figure 2A:
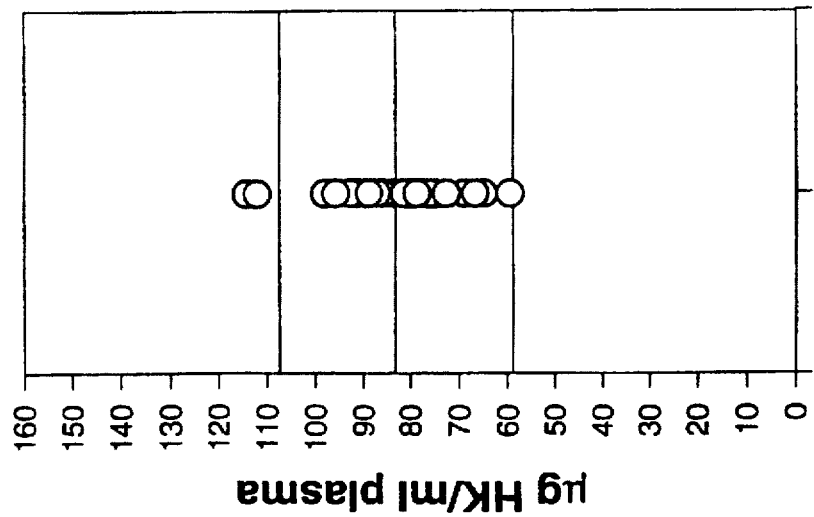
Figure 4:
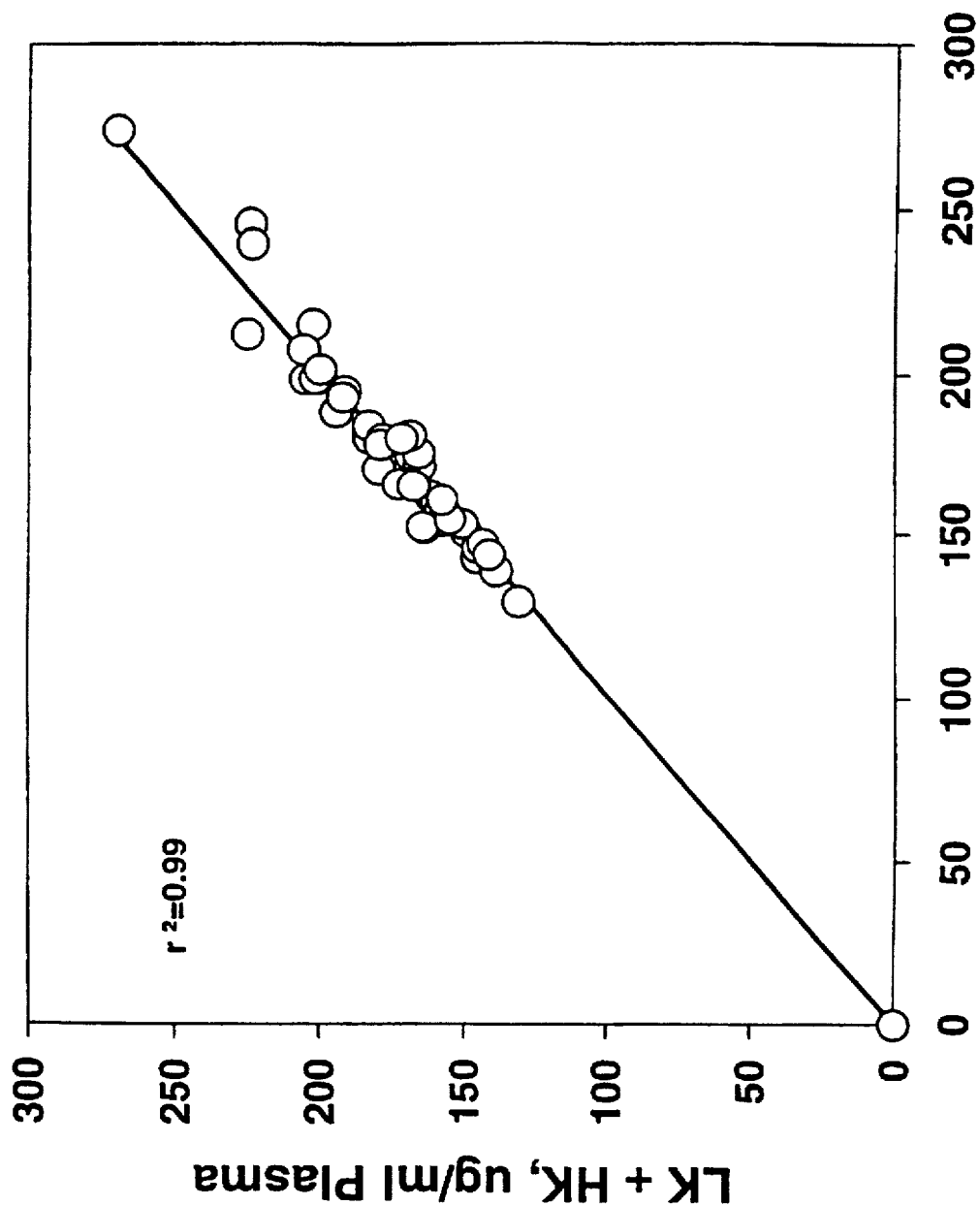
FIG. 4 is a plot of the sum of the HK values (light chain of each) vs. values for TotK (heavy chain) in the plasma of normal donors.

HK-PCFIA was performed using 20 µl of the uncoated CML microspheres (0.25%) and 20 µl of diluted reference plasma or donor plasma. Using a normal pooled plasma containing 80 µg/ml HK, a value of 160 µg/ml was chosen for the 1:50 diluted reference plasma. The standard curve for HK generated with the normal pooled plasma appears as FIG. 1A. HK could be detected in the unknown samples by PCFIA between 50 and 1600 ng/ml. The assay was linear in this range. HK in the 38 normal donors ranged from 59 to 114 µg/ml with a mean of 82 µg/ml (FIG. 2A). These values are similar to HK levels previously reported (Proud et al., *J. Lab. Clin. Med.* 95:563–574, 1980; Syvanen et al., *FEBS Letters* 129:241–245, 1981; Bouma et al., *J. Lab. Clin. Med.* 96:693–709, 1980; Kerbiriou-Nabias et al., *Br. J. Haematol.* 56: 273–286, 1984). When the data from FIG. 2A (HK) were plotted vs. the data from FIG. 2B (LK), a correlation of $r=0.84$, $p<0.0001$ was observed. Two values fell outside the 95% confidence limits (FIG. 3). When the values for LK plus HK were plotted vs. the value for TotK (FIG. 4), there was excellent correlation ($r=0.98$), indicating that the sum of the concentrations determined individually for HK and LK was equal to the concentration of total kininogens that was revealed by the non-discriminating assay (TotK). This finding indicates that the assays for all kininogens are valid and that normal kininogens, for the most part, are intact.

F. Coefficients Of Variation For Kininogen Determinations

The interassay coefficients of variation (c.v.) for HK, LK, and TotK were 3.34, 5.45, and 3.47%, respectively for a sample containing 1 Unit/ml kininogens (where 1 Unit is defined as the amount in 1 ml of normal, pooled plasma) and 5.23, 6.59, and 7.48%, respectively, for a sample containing 0.1 Units/ml. The intraassay coefficients of variation were 4.79, 5.49, and 4.18% for HK, LK, and TotK, respectively, for a sample containing 1 Unit/ml kininogens and 3.76, 1.69, and 3.23%, respectively, for a sample containing 0.7 Units/ml.

G. Determination of Cleaved Kininogen Index (CKI)

A cleaved kininogen index (CKI) was computed as the determined value for HK divided by the difference between the determined total kininogen value and the determined value for LK: HK/(TotK-LK). It is known that the heavy chains of HK and LK can be cleaved between domains 1 and 2 or 2 and 3. However, these cleavages do not affect antigenicity. Therefore, the heavy chain measurement can serve as an "internal standard" for assessing total kininogen concentration. If, however, HK were activated to HKa, which is a more immunoreactive molecule than its intact counterpart, then the CKI would be greater than 1.0. If the surface binding region of HK light chain were cleaved and destroyed and/or if the LKL-1 epitope of LK were cleaved, then the CKI would be less than 1.0. A CKI of 1.0 was calculated for the above assays, thus establishing that the kininogens remain intact during the assay procedure.

H. Determination of Specific Kininogen Level

Total protein was measured with Coomassie Plus Protein Reagent (Pierce Chemical Co.) in all donors in order to calculate "specific kininogen levels" (HK, LK, or TotK divided by total protein). Specific HK ranged from 1.11–2.19 µg/mg total protein with a mean value of 1.46 µg/mg. Specific LK ranged from 1.12–3.06 µg/mg with a mean value of 1.64 µg/mg. Specific TotK ranged from 2.23–5.35 µg/mg with a mean value of 3.12 µg/mg (Table I).

TABLE 1

Mean Values for Kininogens in Normal Donor Plasma[1]

|  | HK µg/ml | LK µg/ml | LK + HK µg/ml | TotK µg/ml | Total Protein mg/ml |
|---|---|---|---|---|---|
| Mean | 82.0 | 92.7 | 174.8 | 175.9 | 56.8 |
| SD | 12.1 | 19 | 26.9 | 29.4 | 6.0 |

|  | Sp. HK µg/mg | Sp. LK µg/mg | Sp. TotK µg/mg | CKI-1 |
|---|---|---|---|---|
| Mean | 1.46 | 1.64 | 3.12 | 1.00 |
| SD | 0.25 | 0.38 | 0.6 | 0.08 |

[1]The data in the table represent the mean values +/− the standard deviation.

EXAMPLE 5

Low Molecular Weight and Total Kininogen Particle

Concentration Fluorescence Immunoassay:

Polyethyleneimine-modified vs. Amino-modified Microspheres

Figure 5A:
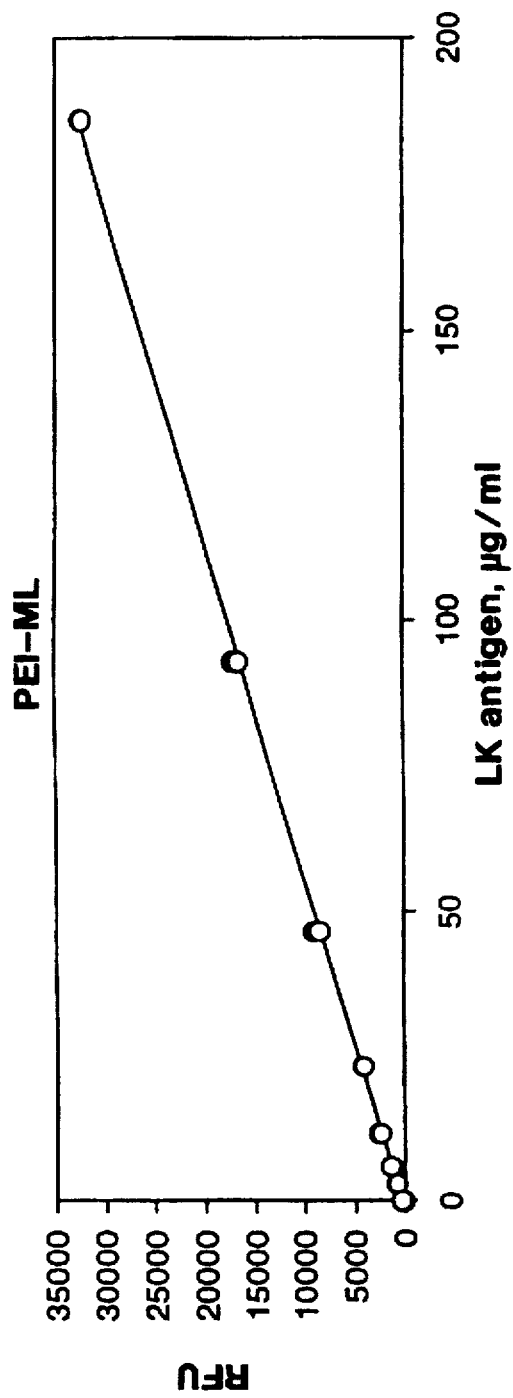
FIGS. 5A, 5B and 5C and 5D are standard curves for LK plasma assays generated from normal pooled plasma using polyethyleneimine-modified latex microspheres (FIG. 5A) and conventional, positively-charged amino-modified microspheres (FIGS. 5B, 5C and 5D).
Figure 5B:
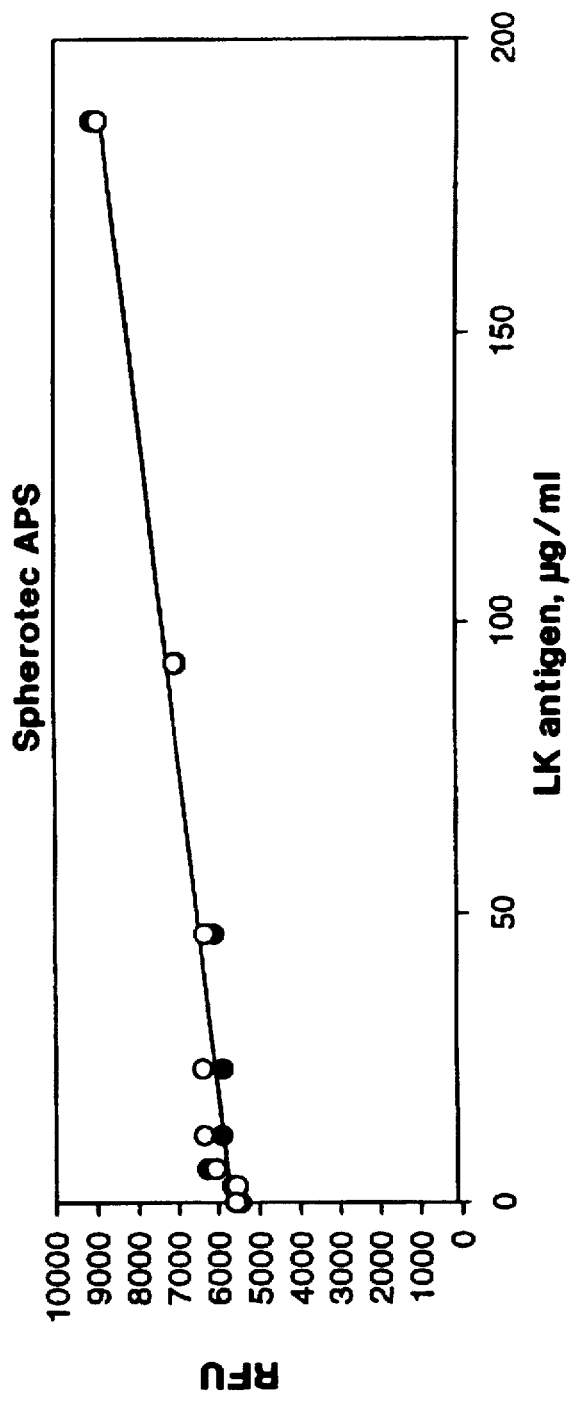
Figure 5C:
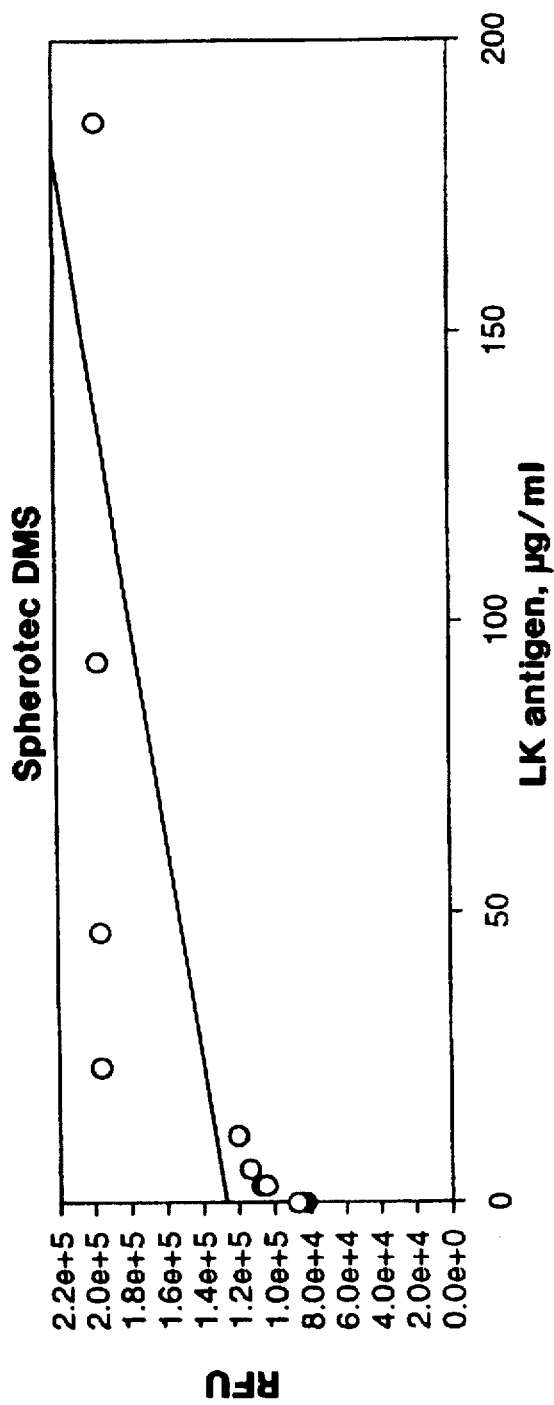
Figure 5D:
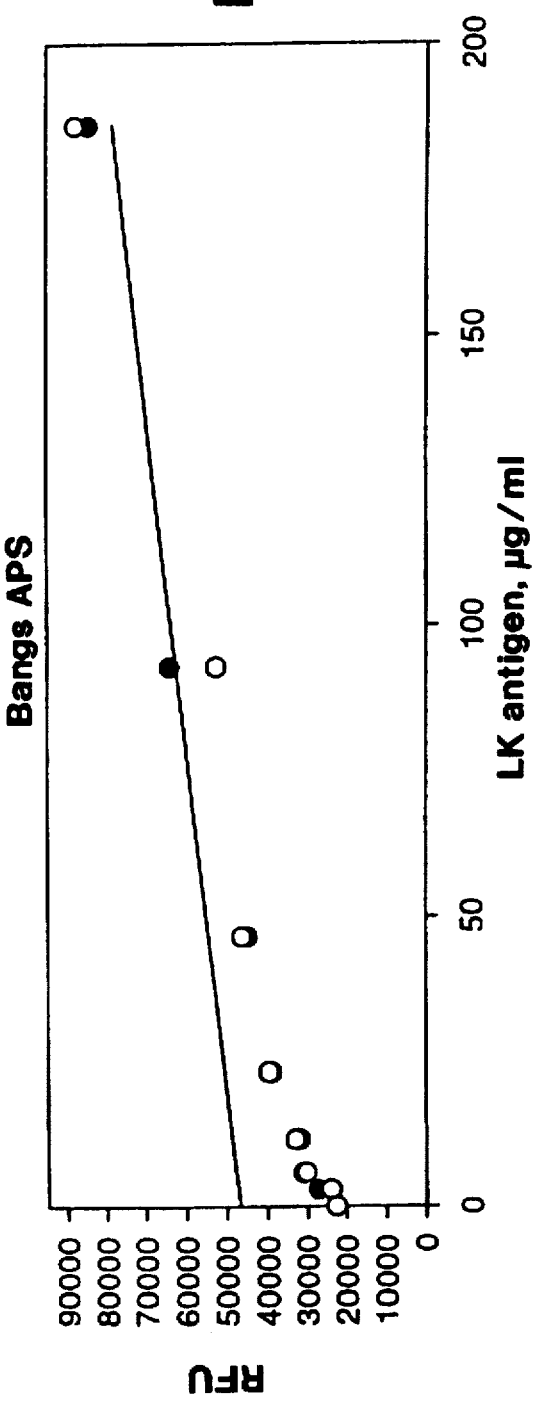
Figure 6C:
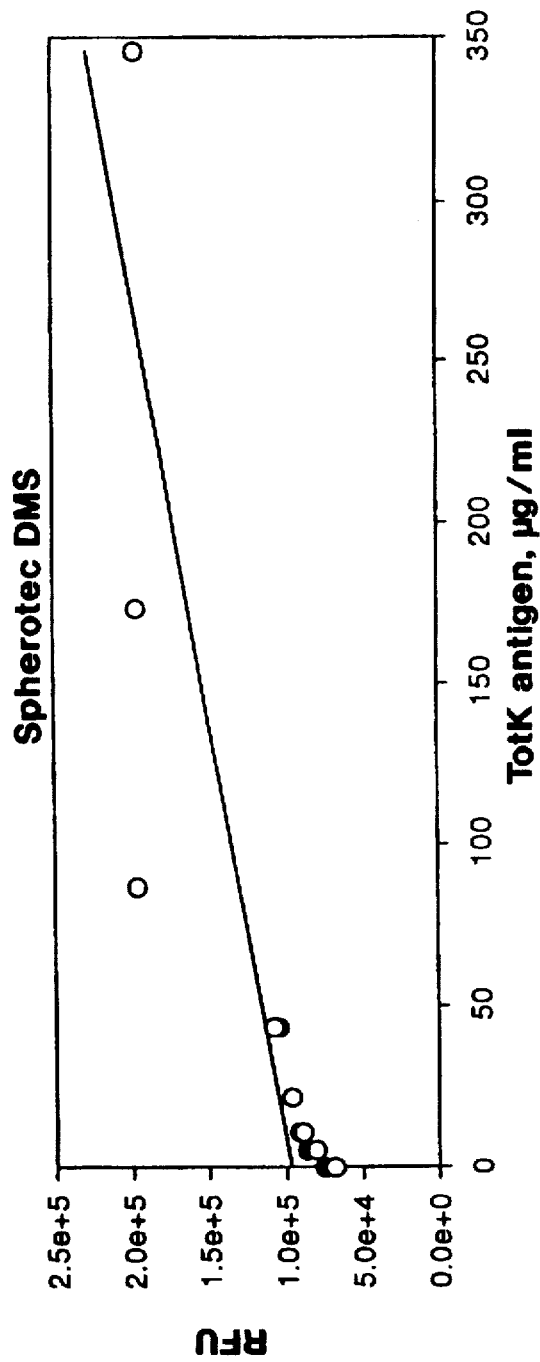
Figure 6D:
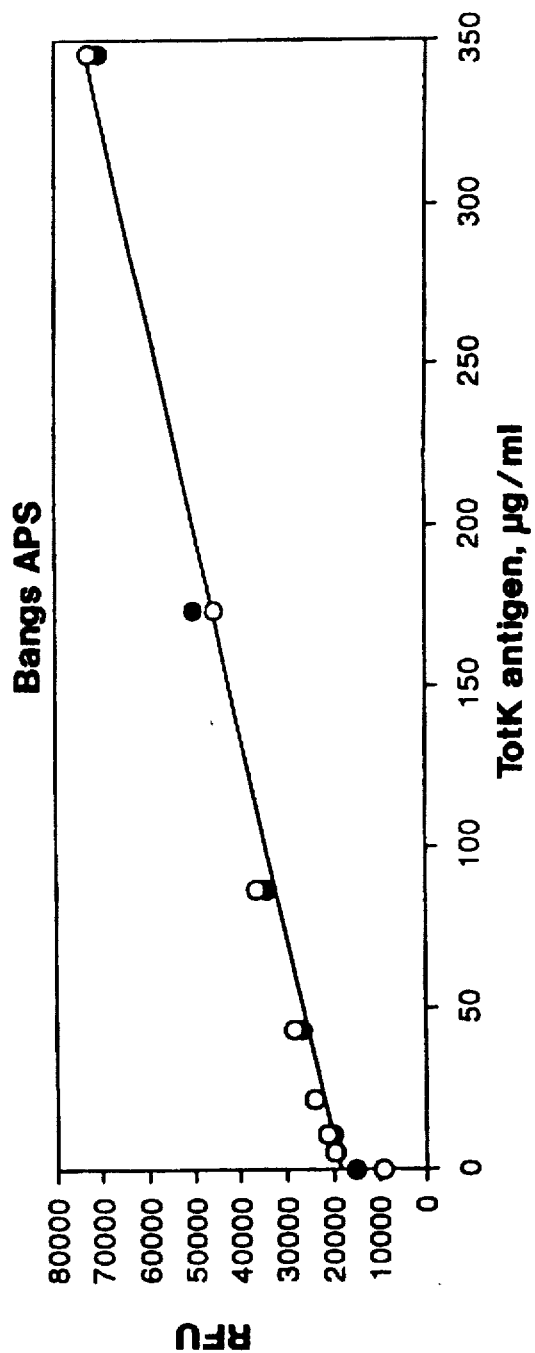

The LK and TotK concentration determination procedures of Example 4 were followed, except that instead of the inventive polyethyleneimine-modified latex microspheres, commercially available amino-modified latex microspheres from two suppliers were used to prepare the MAb-coated microspheres: SPHEROTEC APS and SPHEROTEC DMS (Spherotech, Inc., Libertyville, Ill.); and BANGS APS (Bangs Laboratories, Inc., Carmel, Ind.). As in Example 4, microspheres were coated with MAb LKL-1, which is specific for the LK light chain. Other microspheres were coated with MAb 2B5, which is directed to the common heavy chain of HK and LK. Inventive polyethyleneimine-modified microspheres generated by polyethyleneimine modification of carboxylate-modified latex microspheres according to the present invention (PEI-ML) were also coated with LKL-1 or 2B5 and used for comparison. Standard curves were generated with normal pooled human plasma, as described in Example 4. Both LK (FIG. 5A) and TotK (FIG. 6A) standard curves were linear with the inventive PEI-ML microspheres and had little to no background, indicating no non-specific binding of fluoresceinated antibody tracer. The SPHEROTEC APS microspheres produced a linear assay with TotK (FIG. 6B) but had less than ½ the binding capacity of PEI-ML (Fig.6A). However, in the LK assay, SPHEROTEC APS microspheres produced a high background and a signal to noise ratio of <2.0, indicating that most of the signal in the LK assay was due to non-specific adsorption of HK and/or detector antibody to the microspheres (FIG. 5B). The SPHEROTEC DMS microspheres were totally unsuitable because they produced an extremely high background in both the LK and TotK assays (FIG. 5C, 6C). This result suggests that the tracer is non-specifically adsorbing to the microspheres. The BANGS APS microspheres exhibited a high background in both the LK (FIG. 5D) and TotK (FIG. 6D) assays and a signal to noise ratio less than 4.0. The BANGS APS curves were similar for both assays, suggesting that both HK and LK were binding in addition to non-specific binding of the tracer.

To confirm non-specific adsorption of HK and/or tracer to the microspheres, the same microspheres were incubated with a high concentration of purified HK (527 µg/ml) and the blank values (zero HK) were subtracted from each. PEI-ML bound less than 2% of the HK. Both SPHEROTEC APS and SPHEROTEC DMS bound HK and/or tracer. The values for purified HK were higher than the highest value on their respective standard curves even after the high tracer background was subtracted. BANGS APS bound 30% of the HK in addition to a sizable amount of tracer.

Of the four types of microspheres tested, only the inventive PEI-ML microspheres had a negligible background, produced a linear assay, and bound negligible amounts of HK.

EXAMPLE 6

Low Molecular Weight Kininogen Determination in Crevicular Fluid

A. Collection Of Crevicular Fluid From Patients With Periodontal Disease

Crevicular fluid (10 µl) was collected from patients, undergoing routine treatment at Temple University School Of Dental Medicine, Philadelphia, P , after obtaining written, informed consent. The fluid was collected with a PERIOTRON STRIP (Pro Flow, Amityville, N.Y.) from patients with active periodontal disease and periodontal patients after the disease had been treated where inflammation was no longer evident. The PERIOTRON STRIP was immediately placed into a microcentrifuge tube containing 50 µl 10% protease inhibitor cocktail and frozen at −70° C. These samples were diluted 1:2 for PCFIA so that the final dilution was 1:12.

B. Detection Of HK and LK in Crevicular Fluid

Crevicular fluids from 8 patients with active periodontal disease were assayed for HK and LK. We found HK and LK in three of the samples whereas there was no detectable kininogens in the other five samples (Table 2). In two of the samples, the HK and LK appeared to be moderately cleaved and in one of the samples, the HK and LK were extensively cleaved (CKI=0.59) (Table 2). Six patients with periodontal lesions that had been treated and where inflammation was not evident did not have detectable kininogens (data not shown).

TABLE 2

Evaluation Of Kininogens From Crevicular Fluid
(μg kininogens/ml crevicular fluid)

| Patient | HK | LK | LK + HK | TotK | CKI |
|---|---|---|---|---|---|
| 1 | 7.50 | 4.03 | 11.53 | 16.27 | 0.59 |
| 2 | 2.33 | 4.31 | 6.64 | 7.11 | 0.83 |
| 3 | 6.42 | 12.14 | 18.56 | 19.99 | 0.82 |

EXAMPLE 7

Total Kininogen ELISA
A. Preparation of Polyethyleneimine-modified Microplates

A 1 wt. % solution of 0.1 μ diameter carboxy-modified latex particles (SERACOAT® TC3, Seradyn, Inc.) in ethanol was applied to completely fill each well of a virgin polystyrene microplate. (Alternatively, a 96-well tissue culture plate, e.g., MICROTEST III (Falcon Plastics) may be used in lieu of a virgin polystyrene microplate.) After ten minutes, the nonadherent particles of TC3 were discarded and the plate was rinsed with deionized water. The plate was then inverted on paper towels and dried in a warm air oven at 37° C. for 30 minutes. Polyethyleneimine (50% Sigma Chemical Co.) was diluted with deionized water to a concentration of 10% (v/v) and combined with the ingredients in Table 3, in the amounts indicated therein:

TABLE 3

| polyethyleneimine (10%) | 4 ml |
|---|---|
| 0.1M Na₂PO₄, pH 6.0 + 5 mM EDTA | 4 ml |
| H₂O | 30 ml |
| EDC.HCl (48 mg/250 μl) | 2 ml |

The ingredients were combined and all wells were completely filled with the above solution. After two hours, the plates were washed ten times with deionized water and dried at 37° C. for 30 minutes.
B. Attachment of Total Kininogen Monoclonal Antibody Two hundred microliters of monoclonal antibody 2B5, at a concentration of 5 μg/well, was placed in each of the 96 wells, with the following further ingredients of Table 4, in the indicated amounts:

TABLE 4

| 2B5 (2.6 mg/ml) | 228 μl |
|---|---|
| 0.1M Na₂PO₄, pH 6.0 + 5 mM EDTA | 2200 μl |
| H₂O | 19900 μl |
| EDC.HCl (48 mg/250 μl) | 120 μl |

Figure 7:
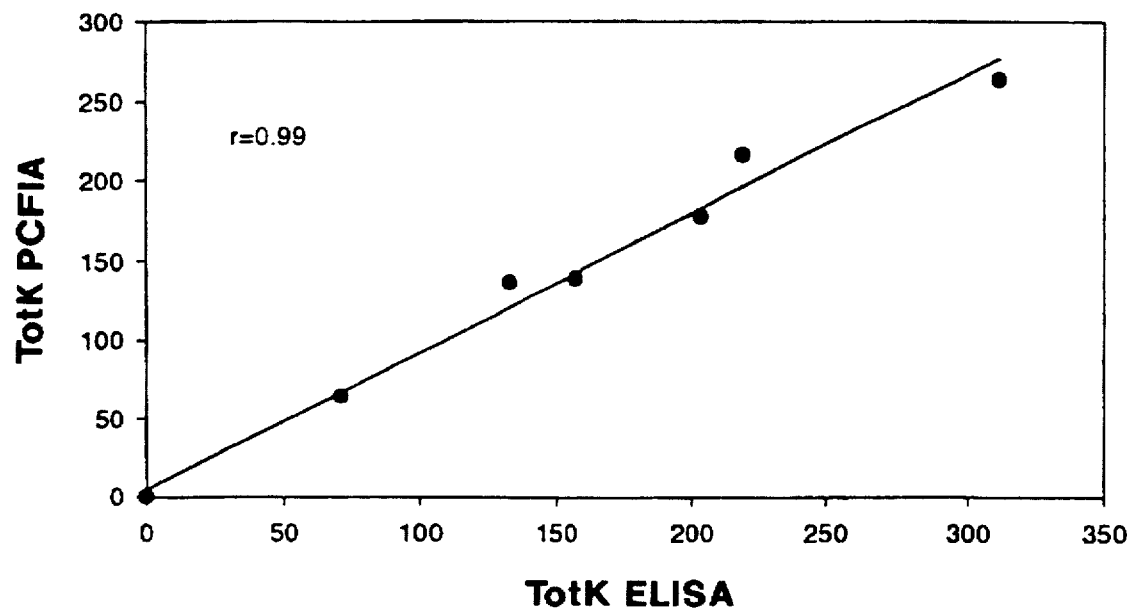
FIG. 7 is a plot of the results of a PCFIA total kininogen assay versus ELISA total kininogen assay results from the total kininogen assay of six plasma samples. An r value of 0.98 was obtained.

The antibody was allowed to incubate anywhere from two hours to overnight. No differences were observed between short and long coupling times.
C. ELISA Procedure Normal pooled human plasma was diluted 1:1000 in PBS-TBI. Serial dilutions in PBS-TBI were made to construct a standard curve. PBS-TBI was used as the blank. Unknown samples to be measured were diluted 1:2000 in PBS-TBI. All determinations were performed in triplicate. Standards and samples (200 μl of each) were placed in a well to which MAB 2B5 was linked. After a 1.5 hour incubation at room temperature, the plates were emptied and washed three times with a wash buffer consisting of 10 mM sodium phosphate, pH 7.0, containing 0.5 M NaCl, 0.02% sodium azide and 0.1% polysorbate 20. Two hundred μl of anti-human HK (Binding Site) diluted 1:1500 in PBS-BSA was placed in each well. After 1.5 hours, the plates were washed, as described above. Anti-sheep IgG-HRP (Binding Site) was diluted 1:200, and 200 μl was applied to each well. After incubation at room temperature for two hours, the plates were washed, as described above. The plates were rinsed once with the same buffer that is used with the substrate, in order to equilibrate the plate to the correct pH and ionic strength. 3,3',5,5'-Tetramethyl benzidine dihydrochloride substrate (Pierce Chemical Co.) was added to the wells at 5-second intervals and allowed to incubate at room temperature. When the optical density of the highest standard was between 0.6 and 0.9, a stopping solution (1M H₂SO₄) was added to terminate the hydrolysis of the substrate. The plates were read at 450 nm on a BIOTEK ELISA reader.
D. Results Seven unknown samples were tested for total kininogen according to the above ELISA procedure. The samples consisted of five normal plasma samples, total kininogen-deficient (Williams) plasma and Fitzgerald Trait plasma. Fitzgerald plasma contains only a trace of HK, but about 50% of the normal LK level. The same seven samples were tested according to the PCFIA TotK method of Example 4D. The results of the PCFIA and ELISA for TotK are plotted in FIG. 7. An r value of 0.98 was obtained. This value indicates that there is excellent correlation between the PCFIA and ELISA assays in the determination of TotK. Williams' plasma was unreactive in this assay.

EXAMPLE 8

Low Molecular Weight Kininogen ELISA
A. Attachment of LK Monoclonal Antibody to Microplates Two hundred μl of monoclonal antibody LKL-1, at a concentration of 5 μg/well, was placed in each of the 96 wells of a microplate prepared in accordance with the procedure of Example 7A. The recipe used to make the antibody solution is as follows:

TABLE 5

| LKL-1 (2 mg/ml) | 287 μl |
|---|---|
| 0.1M Na₂PO₄, pH 6.0 + 5 mM EDTA | 2200 μl |
| H₂O | 19830 μl |
| EDC.HCl (48 mg/250 μl) | 120 μl |

Figure 8:
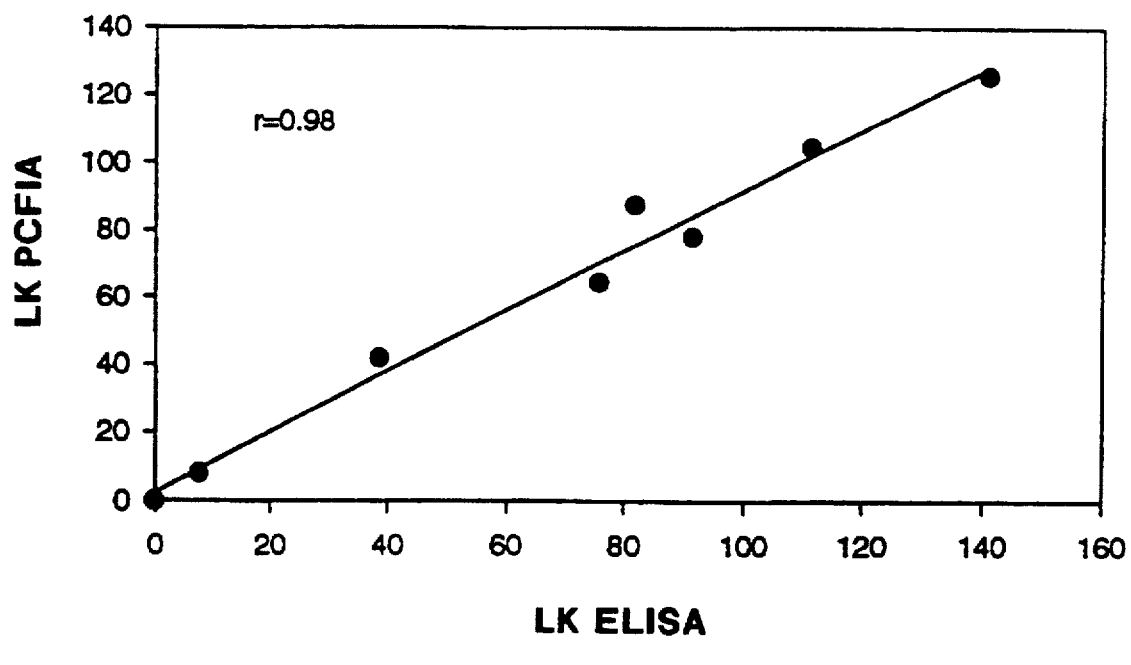
FIG. 8 is a plot of the results of a PCFIA LK assay versus ELISA LK assay results from the LK assay of seven plasma samples. An r value of 0.98 was obtained.

The antibody was allowed to incubate anywhere from two hours to overnight. No differences were observed between short and long coupling times.
B. ELISA Procedure and Results An ELISA procedure similar to the procedure of Example 7C was followed to determine the LK content of the se en samples used in the TotK analysis of Example 7. The above-prepared LKL-1 MAB-coated plates were substituted for the 2B5 MAB-coated plates of Example 7. The same seven samples (i.e., five normal samples, Williams' plasma sanple and Fitzgerald plasma sample) were tested using the LK PCFIA of Example 4C. The results of the PCFIA and ELISA for LK are plotted in FIG. 8. An r value of 0.98 was obtained. This value indicates that there is excellent correlation between the PCFIA and ELISA assays in the determination of LK. Williams'plasma was unreactive in this

EXAMPLE 9

Total Kininogen ELISA and Comparison of Support Surface Modifications

A. Preparation of Polyethyleneimine- modified Microplates

A 96-well virgin polystyrene plate (8×12 well array, Assay Plates. Corning 25880–96 was treated as follows. The wells of one quadrant (3×8=24 wells) were filled with 1% polythyleneimine. The wells of a second quadrant (3×8=24 wells) were filled with 1% polyethyleneimine to which was added 0.52 mM EDC.HCl. To the wells of a third quadrant (3×8=24 wells), was added 1% SERACOAT® TC3 carboxy-modified latex particles in ethanol followed by 1% polyethylenei mine. To the wells of a fourth quadrant (3×8=24 wells) were added 1% SERACOAT® TC3 carboxy-modified latex particles in ethanol, followed by 1% pc lyethyleneimine to which was added 0.52 mM EDC.HCl. The wells of the four quadrants thus contained (1) a passively adsorbed coating of polyethyleneimi e, (2) a coating of polyethyleneimine covalently coupled to the plate surfa by treatment with EDC.HCl, (3) a coating of carboxy-modified late particles to which a coating of polyethyleneimine has been passively adsorbed, or (4) a coating of carboxymodified latex particles to which a coating of polyethyleneimine has been covalently attached by treatment with EDC.HCl. The thus-treated plate was allowed to stand for two hours. The excess liquid was poured out and the thuscoated wells were washed with deionized H$_2$O ten times. The plate was then inverted on top of a paper towel and placed in a 37° C. air oven to evaporate any residual liquid.

B. Attachment of Total Kininogen Monoclonal Antibody

The procedure of Example 7B ) was followed to attach total kininogen monoclonal antibody 2B5 to all wells if the microplate.

C. ELISA Procedure

Figure 9:
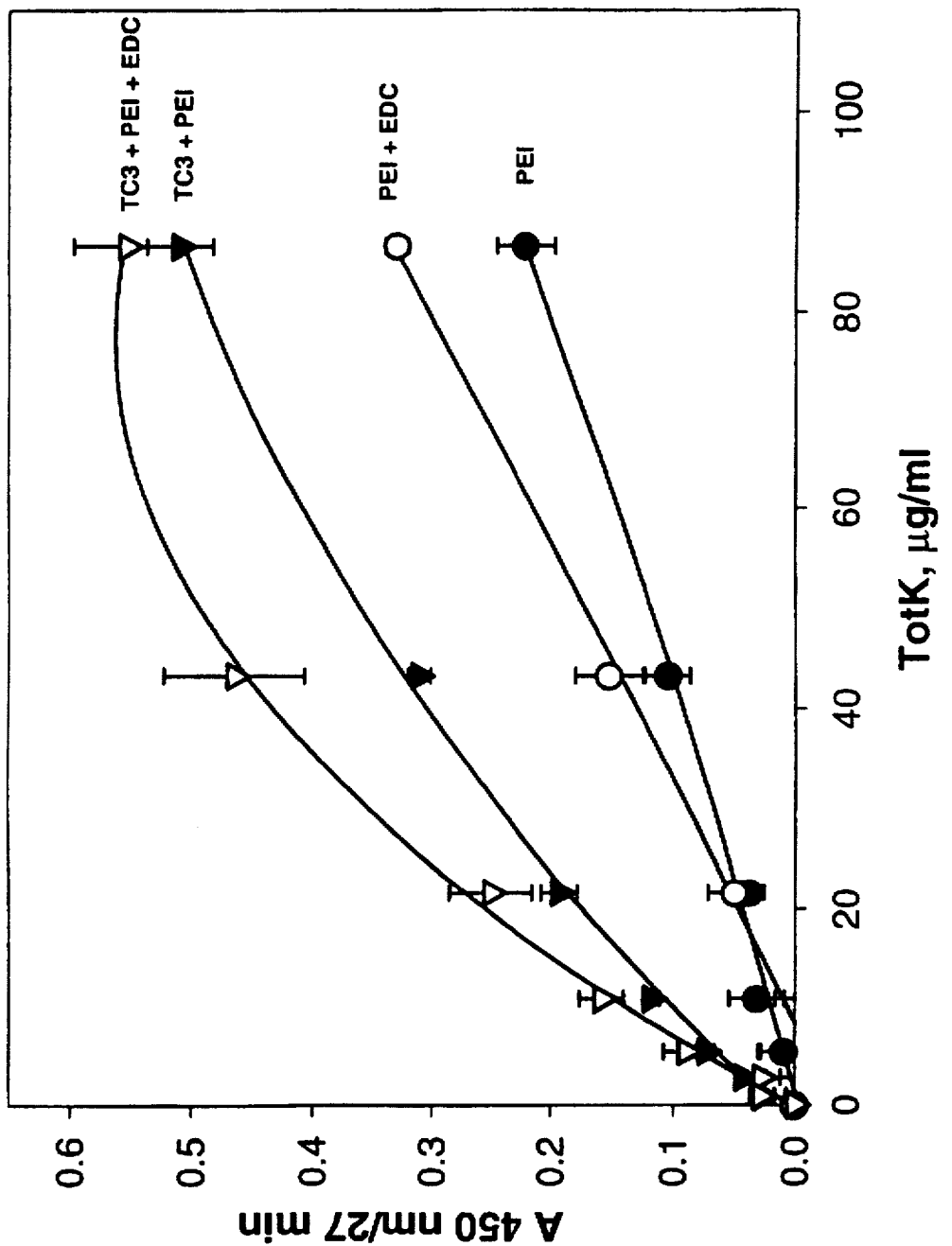
FIG. 9 is a plot of a total kininogen ELISA of samples of known total kininogen concentration carried out in a 96-well microplate wherein the wells were provided with the following coatings prior to attachment of total kininogen monoclonal antibody: a passive coating of polyethyleneimine (solid circles); a coating of polyethyleneimine covalently attached to the well via EDC.HCl (hollow circles); a coating of carboxy-modified latex particles on to which polyethyleneimine was passively adsorbed (solid triangles); a coating of carboxy-modified latex particles to which polyethyleneimine was covalently coupled via EDC.HCl (hollow triangles).

The procedure of Example 7C was followed to generate a total kininogen standard curve for each plate quadrant by adding serial dilutions of normal pooled human plasma diluted in PBS-T BI. PBS-TBI was used as the blank. All determinations were performed in triplicate. The resulting standard curves are shown in FIG. 9: wells passively coated with polyethyleneimine (solid circles); wells to which polyethyleneimine was covalently attached via EDC.HCl (hollow circles); wells containing a coating o carboxy-modified latex particles on to which polyethyleneimine was passive y adsorbed (solid triangles); and wells containing a coating of carboxy modified latex particles to which polyethyleneimine was covalently coup ed via EDC . HCl (hollow triangles). The results indicate that charging the otherwise neutral polystyrene surface with a coating of carboxy-modified latex particles, which are negatively charged, provides for increased binding of pol) ethyleneimine, which in turn allows for more antibody to bind the well. The enhanced antibody binding is most apparent when the negatively charged layer of carboxylate-modified latex and positively charged layer comprising the coating of polyethyleneimine are covalently linked by a covalent coupling agent such as EDC.

EXAMPLE 10

High Molecular Weigh Kininogen ELISA Using Microplate Coated with Carboxy-modified Latex A. Preparation of Polyethyleneimine- modified Microplates A 1 wt. % solution of 0.1 µ diameter carboxy-modified latex particles (SERACOAT® TC3, Seradyn, Inc.) in ethanol was applied to completely fill each well of a MICROTEST III 96-well tissue culture plate (Falcon Plastics). After ten minutes, the nonadherent particles of TC3 were discarded and the plate was rinsed with deionized water The plate was then inverted on paper towels and dried in a warm air oven 37° C. for 30 minutes.

B. ELISA Procedure

Normal pooled human plasma was diluted 1:1000 in PBS-TBI. Serial dilutions in PBS-TBI (1:2) were made to construct a standard curve. PBS-TBI was used as the blank. Unknown samples (Williams plasma and Fitzgerald plasma) to be measured were diluted 1:2000 in PBS-TBI. Standards and samples (200 µl of each) were placed n the microplate wells. After a 1.5 hour incubation at room temperature, the plates were emptied and washed three times with a wash buffer consisting of 10 sodium phosphate, pH 7.0, containing 0.5 M NaCl, 0.02% sodium azide and 0.1% polysorbate 20. Two hundred µl of sheep anti-human HK (Binding S diluted 1:1500 in PBS-BSA was placed in each well. After 1.5 hours, the plates were washed, as described above. Donkey anti-sheep IgG-HRP (Binding Site) was diluted 1:200, and 200 µl was applied to each well. After incubation at room temperature for 1.5 hours, the plates were washed, as described above. The plates were rinsed once with 200 µl of the same buffer that is used with the substrate, in order to equilibrate the plate to the correct pH and ionic strength. Two hundred µl of 3.3',5.5'-Tetramethyl benzidine dihydrochlori Se substrate (Pierce Chemical Co.) was added to the wells at 5-second intervals and allowed to incubate at room temperature. When the optical density of the highest standard was between 0.6 and 0.9, 100 µl of a stopping solution (1M H$_2$SO$_4$) was added to terminate the hydrolysis of the substrate. The plies were read at 450 nm on a BIOTEK ELISA reader.

C. Results

Figure 11:
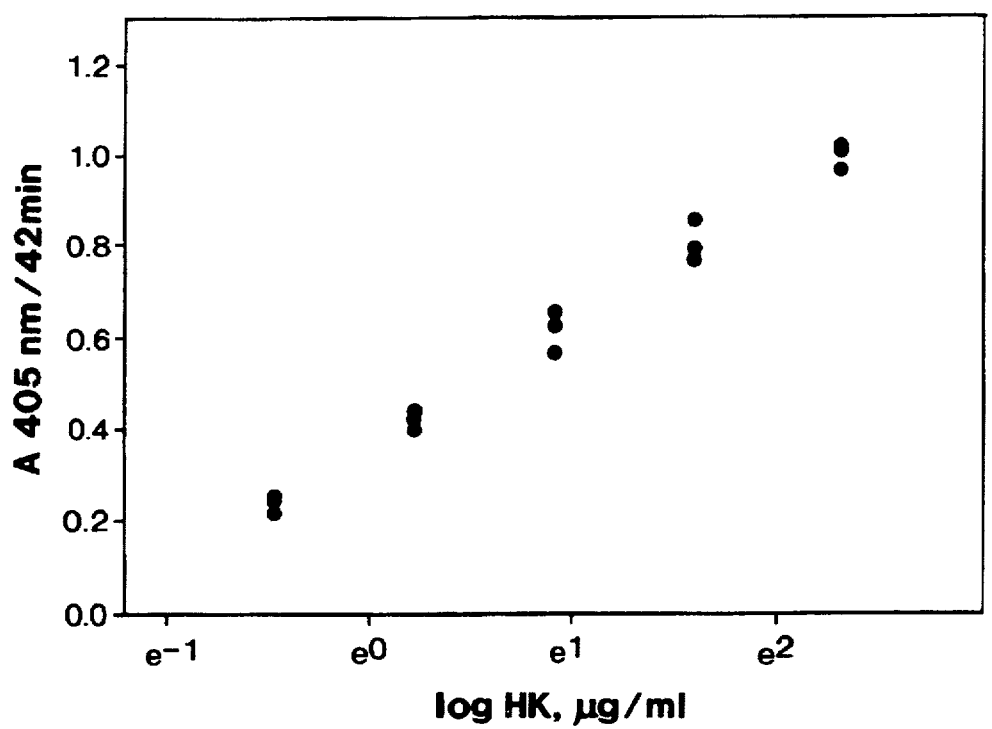
FIG. 11 is a standard curve for an HK plasma ELISA, generated from normal pooled plasma using microplates coated with carboxylate-modified latex as a solid support for capturing HK.

The data from the serial dilutions of the normal pooled plasma are plotted in FIG. 11, which comprises a standard curve for HK concentration in plasma. Williams plasma. The standard curve was then used to determine the HK values of the Williams plasma and Fitzgerald plasma samples. The value for Williams plasma HK was zero. The value for Fitzgerald plasma HK was about 7 µg/ml. These values are in agreement with Williams and Fitzgerald HK values determined by PCFIA.

EXAMPLE 11

Preparation of Polyethyleneimine-modified Microplates:

Effect of Support Surface Modification on Plasma Contact Activation

A. Microplate Coating

Six Falcon MICROTEST III tissue culture plates were treated as follows. Two plates were coated with Composition A. Two plates were coated with Composition B. Composition A and Composition B are shown in Table 6 Two plates were left untreated.

TABLE 6

|  | Composition A | Composition B |
| --- | --- | --- |
| polyethyleneimine (10%) | 4 ml | 4 ml |
| 0.1M Na$_2$PO$_4$, pH 6.0 + 5 mM EDTA | 4 ml | 4 ml |
| H$_2$O | 32 ml | 30 ml |
| EDC.HCl (48 mg/250 µl) | 0 | 2 ml |

The plates were incubated at room temperature over the weekend. The plates were then washed 10 times with deionized water and dried at 35° C. for 30 minutes.

B. Testing the Coating Efficiency

In wells G 11 and 12 of each plate, were placed 5 μl normal pooled plasma and in wells H 22 and 12 of each plate, were placed 5 μl buffer (10 mM sodium phosphate, pH 7.4 containing 150 NaCl). The samples were incubated for exactly 15 minutes at room temperature before adding 150 μl buffer. Finally, 50 μl of the kallikrein synthetic substrate S-2302 (4 mM) (Chromogenix, Inc.) was added to test for kallikrein formation. An IMMULON 2 ELISA plate received plasma and S-2302 in the sane manner. After 40 minutes, 100 μl of 4% citric acid was added to quench the reaction. All microplates were read on a Bio-Tek model 411 ELISA Reader at $A_{405}$ nm. The results are set forth in Table 7.

TABLE 7

| Plate | Absorbance @ 405 nm, 40 minutes |
| --- | --- |
| IMMULON 2 plate | 0.045, 0.049 |
| Composition A-coated tissue culture plate | 0.031, 0.032 |
| Composition B-coated tissue culture plate | 0.027, 0.020 |
| uncoated tissue culture plate | 0.744, 0.820 |

Contact activation of the plasma, as evidenced by extensive kallikrein generation, proceeded in the wells f the uncoated Falcon MICROTEST III culture plate due to the plate's negative surface charge. Kallikrein formation was negligible in the polyethylenimine-coated plates, demonstrating that polyethyleneimine adequately masks negative surface charges. This indicates that certain microplates and vessel otherwise unsuitable for use in blood analyses and procedures where blood comes into contact with the surface for extended periods, due to the presence of negative surface charges, may now be employed in blood assays and other procedures provided they are first coated with polyethyleneimine, preferably E polyethyleneimine coating applied with a covalent coupling agent such as EDC.

EXAMPLE 12

Goat PCFIA

A. Preparation of Goat IgG-Coated Microspheres

Polyethylene-modified microsphetes prepared according to Example 1 were coated with anti-goat IgG (Sigma Chejn. Co.) at a concentration of 0.1 mg/ml antibody by incubating the mixture of Table 8 overnight at room temperature on a rotating mixer:

TABLE 8

| | |
| --- | --- |
| Microspheres (10%) | 100 μl |
| 100 mM $Na_2PO_4$, pH 6.0 + 5 mM EDTA | 100 μl |
| anti-goat IgG (2 mg/ml) | 100 μl |
| $H_2O$ | 1590 μl |
| EDC.HCl (48 mg/250 ml) | 10 μl |

The treated microspheres were then blocked for 30 minutes with 10 mg/ml BSA, centrifuged and washed with water, and resuspended in a final volume of 4 ml PBS-Tween.

B. Goat IgG PCFIA

Figure 10:
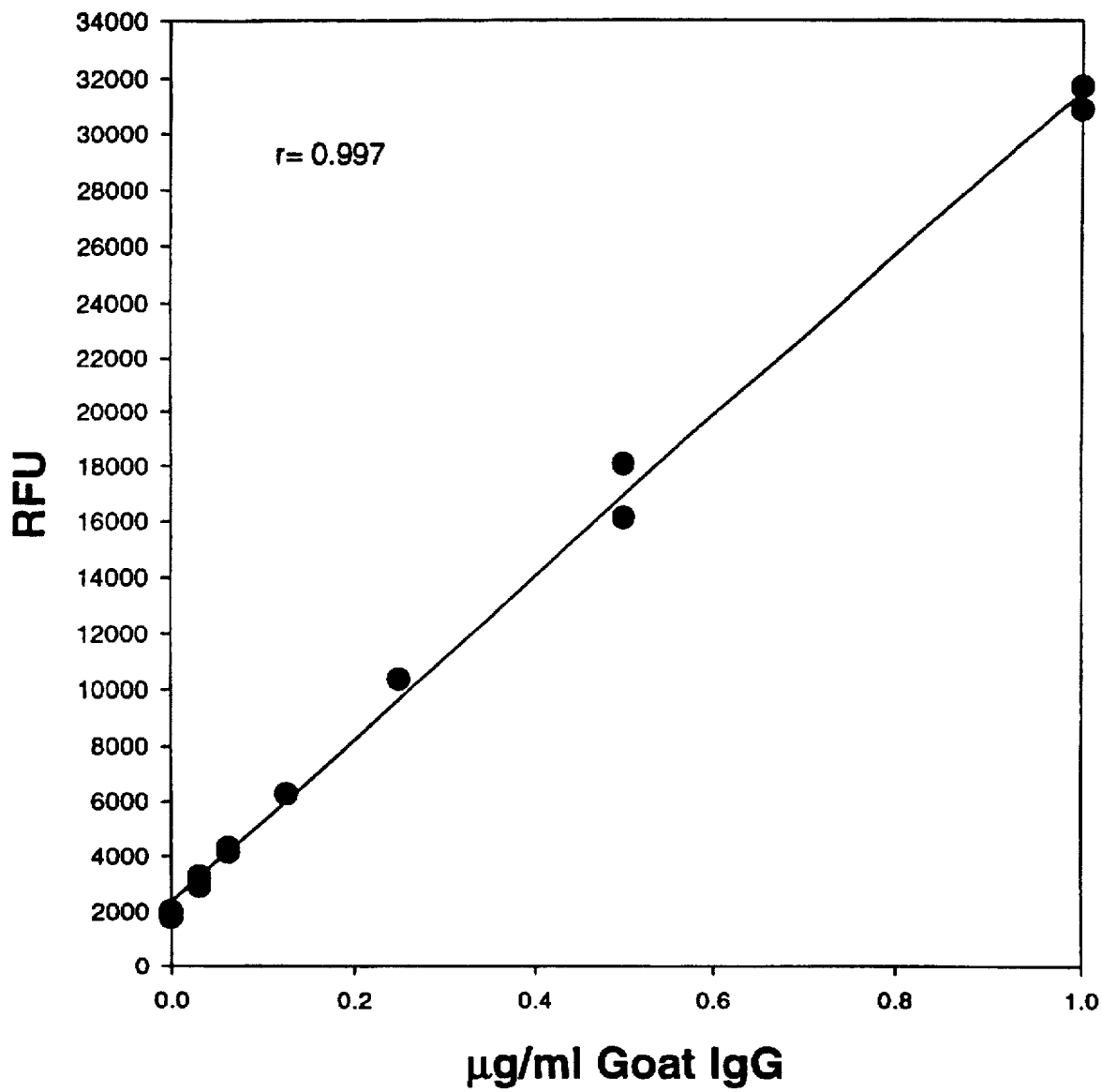
FIG. 10 is a plot of a PCFIA determination of goat IgG constructed from serial dilutions of purified goat serum.

A PCFIA standard curve utilizing r serial dilutions of purified goat IgG was generated spanning an IgG concentration of 0 to 1000 ng/ml. The diluent for preparation of the samples for the standard curve was PBS-Tween-BSA filtered with a 0.2 μm syringe filter. Twenty ttl microspheres were added to each well of a 96-well microplate, followed by 20 μl of diluted sample or reference standard. After 20 minutes at room temperature, 20 μl of an FITC-labeled donkey anti-goat IgG (anti-goat IgG-FITC) solution prepared by diluting commercially available anti-goat IgG-FITC 1:100 in PBS-Tween-BSA containing 20% donkey serum was added to the wells as a tracer. The mixture was incubated for 20 minutes. The plate was then read in an FCA as in Example 1, at an instrument gain of 5. The data appears in FIG. 10.

EXAMPLE 13

Antibody Screening with Polyethyleneimine-modified Microspheres

A. PCFIA Screening of Mouse Serum-1

The peptide Ac-Cys-Glu-Tyr-Lys Gly-Arg-Pro-Pro-Lys-Ala-Gly-Ala-Glu-Pro-Ala-Ser-Glu-Arg-Glu-Val-Ser-$NH_2$. 4TFA, synthesized by Commonwealth Biotechnologies, Inc. (Richmond, Va.) was coupled to keyhole limpet hemocyanin and used as an immunogen in raising antisera in mice. The same peptide, coupled to ovalbumin using the coupling reagent IMJECT®-Maleimide Activated Carrier Protein (Pierce Chemical Co., Rockford, Ill.) was used to make a solid phase antigen to screen the antibodies by PCFIA.

The ovalbumin-peptide conjugate was covalently attached to polyethyleneimine-modified CML mirospheres according to the attachment procedure of Example 2. The petide-linked polyethyleneimine-modified microspheres were then used to screen the serum of five mice immunized with the ovalbumin-peptide conjugate, using a particle concentration fluorescence immunoassay (PCFIA) according to Example 4. The screening was performed on pre-immune serum, serum collected after initial immunization, and serum collected after a first boost with immunogen. The peptide-coated microspheres (20 μl of 0.25%) were placed in each PCFIA plate. The mouse serum was diluted 1:1000 with PCFIA diluent, according to Example 4 above, and 20 μl were placed in the wells containing the microspheres. After 15 minutes, the plate was washed and 20 μl 1:50 diluted anti-mouse IgG-FITC (Sigma Chemical Co.) was added and incubated 15 minutes. The plate was washed and read in a Fluorescence Concentration Analyze, as in Example 4. The data is set forth in Table 9.

TABLE 9

| Relative Fluorescence Units in Mouse Serum | | | |
| --- | --- | --- | --- |
| Mouse # | Pre-immune | Immunization | 1st Boost |
| 1 | 0 | 6318 | 21367 |
| 2 | 0 | 4208 | 33209 |
| 3 | 0 | 25013 | 44622 |
| 4 | 0 | 20403 | 40988 |
| 5 | 0 | 22672 | 10469 |

Total mouse IgG was also measured on all samples using commercially available reagents, as in Example 2, SO that "specific anti-LK IgG" (RFU divided by total mouse IgG) could be calculated. There were between 6318 and 44622 specific anti-LK IgG in the serum of the mice after immunization. This is compared to a value of 83304 teat was determined for ascites from the hybridoma producing MAb LKL-1.

B. PCFIA Screening of Mouse Hybridoma Culture Supernatant

One or more of the immune ice were sacrificed. The spleens were removed and splenocytes were fused ith myeloma cells to prepare hybridomas according to conventional hybridoma procedures. The hybridoma tissue culture supernatants were then screened using PCFIA for antibody reactivity to the peptide-linked polyethyleneimine-modified microspheres. There was no measurable fluorescence in the p e-immune samples. Most of the 500 hybridomas screened produced no fluorescence. Several samples had low RFUs (<10,000). Only ten samples provided relative fluorescence units (RFUs) between 10,000 and 60,000. The ability to rapidly distinguish, unequivocally, positive from negative hybridomas, facilitated the selection of hybridomas for the next step in monoclonal antibody production. Unlike conventional ELISA procedures currently used to screen hybridoma supernatants, which require several days to complete, more than 500 samples may be screened in just a few hours with PCFIA using the polyethyleneimine-modified microspheres of the invention.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

7. A carrier according to claim 6 wherein the microparticles comprise a carboxylate-modified latex.

8. A carrier according to claim 6 wherein said polyethyleneimine coating has been applied to said microparticles with a coupling agent to covalently couple said polyethyleneimine to said microparticles.

9. A carrier according to claim 8 wherein the coupling agent is a carbodiimide.

10. A carrier according to claim 9 wherein the coupling agent is 1-ethyl-3-(3-dimethylaminopropyl)carbodiimide, or salt thereof.

11. A carrier according to claim 6 wherein the solid support comprises a microplate.

12. A method of treating a negatively charged polymeric surface to inhibit contact activation of plasma by said surface consisting essentially of coating said surface with polyethyleneimine.

13. A method of treating a surface of a microplate comprising a negatively charged polymeric material to

I claim:

1. A solid support for an immunoassay comprising
   (a) a microplate comprising a negatively charged polymeric material;
   (b) a coating of polyethyleneimine on said microplate.

2. A support according to claim 1 wherein the polyethyleneimine coating has been applied to said microplate with a coupling agent to covalently couple said polyethyleneimine to said microplate.

3. A support according to claim 2 wherein the coupling agent is a carbodiimide.

4. A support according to claim 3 wherein the coupling agent is 1-ethyl-3-(3-dimethylaminopropyl)carbodiimide, or salt thereof.

5. A support according to claim 4 wherein the negatively charged polymeric material comprises a modified polystyrene.

6. A carrier for an immunoassay comprising
   (a) a solid support;
   (b) a layer of microparticles coated on said solid support, said microparticles being formed of a negatively charged polymeric material;
   (c) a coating of polyethyleneimine on said microparticles.

inhibit contact activation by said surface comprising coating said surface with polyethyleneimine.

14. A method according to claim 13 wherein the polyethyleneimine coating is applied to said microplate with a coupling agent to covalently couple said polyethyleneimine to said microplate.

15. A method according to claim 14 wherein the coupling agent is a carbodiimide.

16. A method according to claim 15 wherein the coupling agent is 1-ethyl-3-(3-dimethylaminopropyl)carbodiimide, or salt thereof.

17. A solid support for a high molecular weight kininogen assay comprising:
    (a) a microplate; and
    (b) a coating of a negatively charged polymeric material on said microplate.

18. A solid support according to claim 17 wherein the coating on said microplate comprises a layer of microparticles formed of a negatively charged polymeric material.

19. A solid support according to claim 18 wherein the microparticles comprise a carboxylate-modified latex.

20. The carrier according to claim 7 wherein the microparticles are up to about 0.1 μm in diameter.

21. The support according to claim 18 wherein the microparticles are up to about 0.1 μm in diameter.

22. The method of claim 12 wherein the polyethyleneimine coating has been applied to said surface with a coupling agent to covalently couple said polyethyleneimine to said surface.

23. The method of claim 22 wherein the coupling agent is a carbodiimide.

24. A method according to claim 23 wherein the coupling agent is 1-ethyl-3-(3-dimethylaminopropyl)carbodiimide, or salt thereof.

25. The method according to claim 13 consisting essentially of coating said surface with polyethyleneimine.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( x i ) SEQUENCE DESCRIPTION: SEQ ID NO:1:

```
Cys Glu Tyr Lys Gly Arg Pro Pro Lys Ala Gly Ala Glu Pro Ala Ser
1               5                   10                  15

Glu Arg Glu Val Ser
            20
```